US012440230B2

(12) United States Patent
Gamba et al.

(10) Patent No.: US 12,440,230 B2
(45) Date of Patent: Oct. 14, 2025

(54) DEVICES AND METHODS FOR REMOVING MATERIAL FROM A PATIENT

(71) Applicant: Penumbra, Inc., Alameda, CA (US)

(72) Inventors: Jorge Gamba, Jacksonville, FL (US); Eric Sauvageau, Jacksonville, FL (US); Michael Schaller, Louisville, CO (US)

(73) Assignee: Penumbra, Inc.

( * ) Notice: Subject to any disclaimer, the term of this patent is extended or adjusted under 35 U.S.C. 154(b) by 397 days.

(21) Appl. No.: 17/928,130

(22) PCT Filed: May 27, 2021

(86) PCT No.: PCT/US2021/034429

§ 371 (c)(1),
(2) Date: Nov. 28, 2022

(87) PCT Pub. No.: WO2021/242963

PCT Pub. Date: Dec. 2, 2021

(65) Prior Publication Data

US 2023/0210544 A1 Jul. 6, 2023

Related U.S. Application Data

(60) Provisional application No. 63/150,211, filed on Feb. 17, 2021, provisional application No. 63/030,598, filed on May 27, 2020.

(51) Int. Cl.
*A61B 17/221* (2006.01)

(52) U.S. Cl.
CPC .... *A61B 17/221* (2013.01); *A61B 2017/2215* (2013.01); *A61B 2217/005* (2013.01)

(58) Field of Classification Search
CPC .......... A61B 17/221; A61B 2017/2215; A61B 2217/005; A61B 17/22; A61B 2017/22094
See application file for complete search history.

(56) References Cited

U.S. PATENT DOCUMENTS

| | | | |
|---|---|---|---|
| 5,681,324 | A | 10/1997 | Kammerer et al. |
| 5,814,064 | A | 9/1998 | Daniel |
| 6,663,650 | B2 | 12/2003 | Sepetka et al. |
| 7,780,696 | B2 | 8/2010 | Daniel et al. |

(Continued)

FOREIGN PATENT DOCUMENTS

| | | | |
|---|---|---|---|
| EP | 1629784 | A1 | 3/2006 |
| JP | 2002-502626 | A | 1/2002 |

(Continued)

OTHER PUBLICATIONS

International Search Report and Written Opinion, PCT/US2021/034429, dated Aug. 31, 2021.

(Continued)

*Primary Examiner* — Mohamed G Gabr
*Assistant Examiner* — Khoa Tan Le
(74) *Attorney, Agent, or Firm* — Polsinelli PC

(57) ABSTRACT

A containing element is used to capture material in a blood vessel for removal. The containing element is advanced through the blood vessel or a catheter in a constricted configuration. A control body is coupled to the containing element which assists moving the containing element. In some embodiments, the containing element is used for restricting blood flow within a vessel.

9 Claims, 11 Drawing Sheets

(56) References Cited

U.S. PATENT DOCUMENTS

| | | | |
|---|---|---|---|
| 8,109,941 | B2 | 2/2012 | Richardson |
| 8,940,003 | B2 | 1/2015 | Slee et al. |
| 9,498,604 | B2 | 11/2016 | Dubrul et al. |
| 10,624,659 | B2 | 4/2020 | Gamba et al. |
| 11,589,882 | B2 | 2/2023 | Gamba et al. |
| 2001/0051810 | A1 | 12/2001 | Dubrul et al. |
| 2002/0072764 | A1 | 6/2002 | Sepetka |
| 2005/0228417 | A1 | 10/2005 | Teitelbaum et al. |
| 2006/0047286 | A1 | 3/2006 | West |
| 2006/0155305 | A1 | 7/2006 | Freudenthal |
| 2006/0195118 | A1 | 8/2006 | Richardson |
| 2006/0195137 | A1 | 8/2006 | Sepetka et al. |
| 2008/0125709 | A1 | 5/2008 | Chang et al. |
| 2011/0125181 | A1* | 5/2011 | Brady .............. A61B 17/22031 606/200 |
| 2013/0317589 | A1 | 11/2013 | Martin et al. |
| 2014/0025083 | A1 | 1/2014 | Richardson |
| 2014/0257362 | A1 | 9/2014 | Eidenschink |
| 2016/0220265 | A1 | 8/2016 | Pokorney et al. |
| 2017/0035445 | A1 | 2/2017 | Nguyen |
| 2017/0065299 | A1 | 3/2017 | Gillespie et al. |
| 2017/0086861 | A1 | 3/2017 | Mansfield et al. |
| 2018/0235644 | A1 | 8/2018 | Jaffe et al. |
| 2019/0298396 | A1* | 10/2019 | Gamba ................ A61B 17/221 |
| 2020/0008820 | A1* | 1/2020 | Aboytes ........... A61B 17/12136 |

FOREIGN PATENT DOCUMENTS

| | | | |
|---|---|---|---|
| JP | 2006068527 | | 3/2006 |
| JP | 2011-512900 | A | 4/2011 |
| WO | WO 99/39648 | | 8/1999 |
| WO | WO 2007/110864 | A2 | 10/2007 |
| WO | WO 2020/099386 | A1 | 5/2020 |

OTHER PUBLICATIONS

International Search Report and Written Opinion, PCT/US2019/021943, dated Aug. 26, 2019.

Extended European Search Report, EP19767116.7, dated Dec. 14, 2021.

Japanese Office Action, JP 2021-500017, dated Feb. 21, 2023.

* cited by examiner

DEVICES AND METHODS FOR REMOVING MATERIAL FROM A PATIENT

CROSS-REFERENCE TO RELATED APPLICATIONS

The present application claims priority to U.S. Provisional Patent Application No. 63/150,211 filed Feb. 17, 2021 and U.S. Provisional Patent Application No. 63/030,598 filed May 27, 2020. The contents of the above-mentioned patent applications are hereby incorporated by reference in their entirety.

TECHNICAL FIELD

This disclosure relates generally to the field of surgery, and more specifically to the field of interventional radiology. Described herein are devices and methods for removing material from a patient.

BACKGROUND

Minimally invasive endovascular techniques have come to the forefront in the safe and expeditious use of embolectomy devices for thromboembolic clot extraction. This includes, without limitation, clot extraction to treat neurovascular ischemic stroke, pulmonary embolism, deep vein thrombosis, arterial thrombosis, stone removal, and others. Currently employed devices generally extract the clot using a combination of balloons, graspers, aspiration, and wire retrievers. Many of these devices attempt to remove the clot in vivo by attaching to it and then pulling it through the vascular lumen and out of the body. With these devices the thrombus is typically not fully contained and if fragments of the clot break away, they may become new emboli in the blood stream. That is to say that existing devices typically maintain partial or full exposure of the thrombus within the vascular lumen and when clot extraction is attempted the "bare thrombus" can pose a threat of fragmentation or partial clot dislodgement which can predispose a patient to inadvertent distal embolization, non-target territory embolization or incomplete thrombus extraction.

Additionally, in order to limit the blood flow in the clotted vessel during clot removal, many procedures utilize a variety of flow arrest techniques such as balloon-assisted proximal vessel occlusion to minimize antegrade flow in an effort to exclude distal clot fragmentation during clot extraction. Mechanical or assisted suction techniques are oftentimes utilized simultaneously via the balloon flow arrest catheter to capture any potential embolic debris during clot extraction. However, some existing flow reducing devices such as balloon guide catheters are inherently stiff and difficult to deliver to their target location and are often larger than desired requiring large entry wounds to access the vasculature. Additionally, in some application complete flow arrest is often difficult due to extensive collaterals, such as with neuro thrombectomy and the collateral intracranial vessels (e.g. Circle of Willis), limiting the efficacy and utility of proximal flow arrest and suction in the carotid circulation. Even limited blood flow can create a significant risk of clot fragmentation and distal migration of clot during extraction.

Encasing the occlusive material during removal from the patient's vasculature and providing flow arrest in the vessel during material removal would potentially improve patient outcomes.

SUMMARY

The present invention is directed to devices and methods for removing material from a blood vessel and restricting blood flow. In a specific application, the devices and methods are used to capture and remove an occlusive clot from a patient's vasculature. The device includes a containing element which is constricted and which is advanced to a vascular location. The containing element is then deployed in a position to receive and contain material for removal. A clot retrieving element such as a stent retriever or aspiration may be used to engage the material to be removed and assist in moving the material into the containing element.

The containing element has a distal opening at a distal end and an outer wall extending proximally from the distal opening. The distal opening is moved to an open position to receive the material in an interior chamber formed by the outer wall. The device includes a suction source connected to an aspiration path that runs through a constraining catheter, through the containing element, and through the distal opening of the containing element into the vessel.

A first control body is coupled to the containing element to manipulate the containing element. The first control body advances the containing element through a constraining catheter or through the patient's vasculature. When the containing element is positioned at or near the location where the material is to be removed, the containing element is expanded. The containing element may be moved between constricted and expanded configurations by the application and removal of tension to the containing element through the first control body. A second control body may additionally be coupled to the containing element. Moving the control bodies relative to one another allows for the application of tension to the containing element such that it can be constricted. The containing element has various aspects that allow it to also naturally expand as tension is released from the containing element. The outward expansion pressure of the containing element can be configured to resist collapse from vacuum pressure.

Once the material is contained within the containing element, the containing element can be moved to a closed configuration in which the distal opening is reduced in size to prevent the material from escaping through the distal opening as the containing element is removed and/or moved into another catheter or sheath for removal from the patient. The distal opening may be closed by advancing the control body or retracting the control body proximally.

The foregoing is a summary, and may be limited in detail. The above-mentioned aspects, as well as other aspects, features, and advantages of the present technology are described below in connection with various embodiments, with reference made to the description, claims and accompanying drawings.

DETAILED DESCRIPTION

Figure 1A:
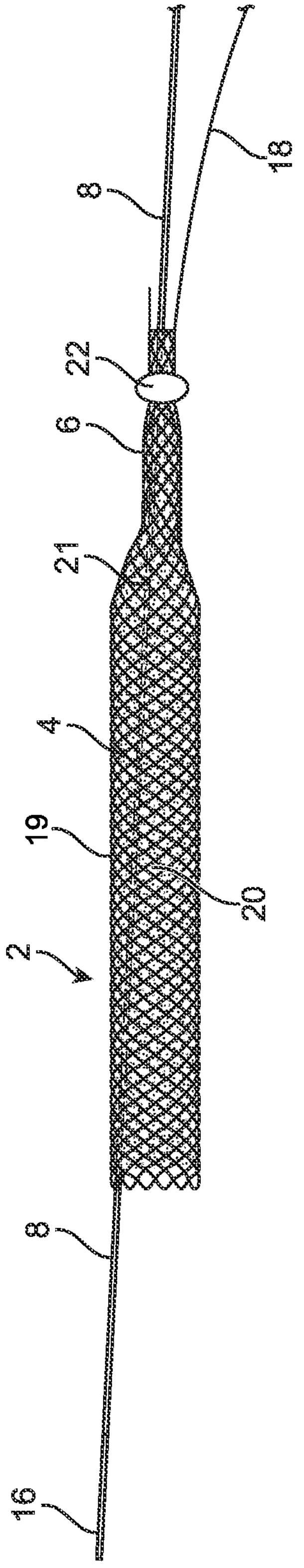
FIG. 1A illustrates an embodiment of a device according to the present disclosure in a side view.

In FIG. 1A, a device 2 to remove material from a blood vessel and/or restrict blood flow in the vessel is shown. The device 2 includes a containing element 4 formed at its proximal end to a containing element catheter 6. The device 2 is shown in a generally expanded configuration with the containing element 4 unrestricted and including a distal opening 7. The containing element 4 includes a membrane 5 that surrounds an interior chamber 20. This embodiment of the device 2 further includes a filament 10 at the distal portion that is engaged to the containing element 4 through a series of loops 12 at the distal opening 7. The filament 10 connects to a distal control body 8 at the filament connection 14. The distal control body 8 runs through the interior chamber 20 of the containing element 4 and through the containing element catheter 6. The distal control body 8 further has an extension tip 16 that extends distally beyond the distal portion of the containing element 4.

The various construction and elements of an embodiment of the device 2 will be described in greater detail below. Aspects of the present invention are described with reference to a single or limited number of embodiments; however, it is understood that all features, aspects and methods are incorporated into all applicable embodiments described herein even though not expressly mentioned or set forth. For example, the detailed description below is primarily in directed to neuro thrombectomy applications, including dimensions such as diameters, lengths, thicknesses etc. In other applications these dimensions may be different depending on such factors as the target vessel size and clot size. Any ranges provided in the application are exemplary only and should not limit the scope or application of the device or methods.

Figure 1B:
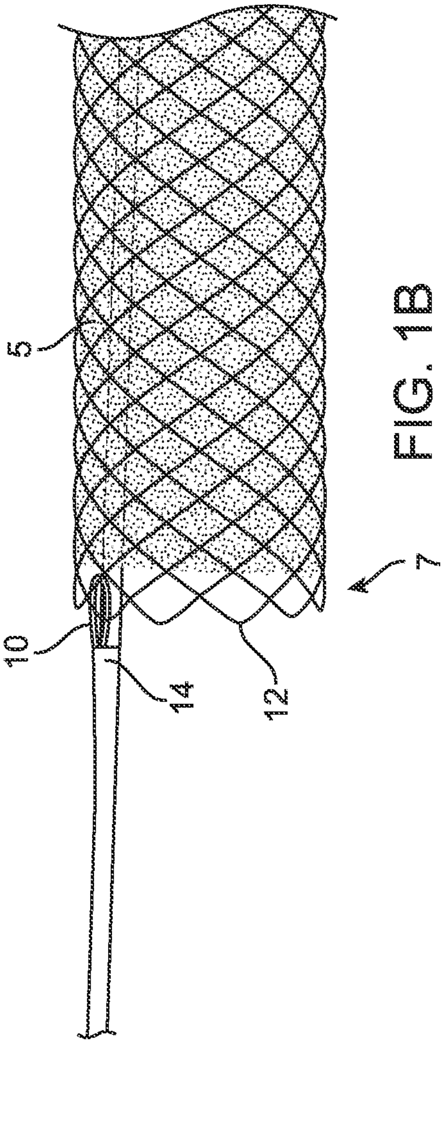
FIG. 1B illustrates a detailed view of a containing element distal opening of the device of FIG. 1A.

In FIG. 1A, a part of device 2 is shown with the distal opening 7 expanded. The containing element 4 is an expandable tube that can be made partly of a metallic or polymeric braid and forms an interior chamber 20 when expanded. The braid can have a polymeric membrane 5 on the inner or outer surface to surround part or all of the interior chamber 20. The containing element 4 includes a containing element catheter 6 at the proximal end that transitions the interior chamber 20, which is defined by the outer wall 19, to a smaller tubular region. The containing element catheter 6 can include a sealing surface 22 for sealing on the inner lumen of a constraining catheter as will be shown below. The distal portion of the containing element 4 can be connected via a filament 10 to a distal control body 8 that runs through the containing element 4 and through the containing element catheter 6. The distal control body 8 can include an extension tip 16 that provides a transition between a flexible distal region and a stiffer region near the filament connection 14. In FIG. 1B, the distal opening 7 of the containing element 4 is shown in greater detail. The containing element 4 can include atraumatic features at its distal opening 7 including one or more loops 12. The filament 10 can be connected to the containing element 4 by weaving through the one or more loops 12. The containing element catheter 6 can be attached to a proximal control body 18 which can be a wire or tube that runs within the constraining catheter. The operation of device 2 will now be described in more detail.

Figures 2A, 2B, 2C:
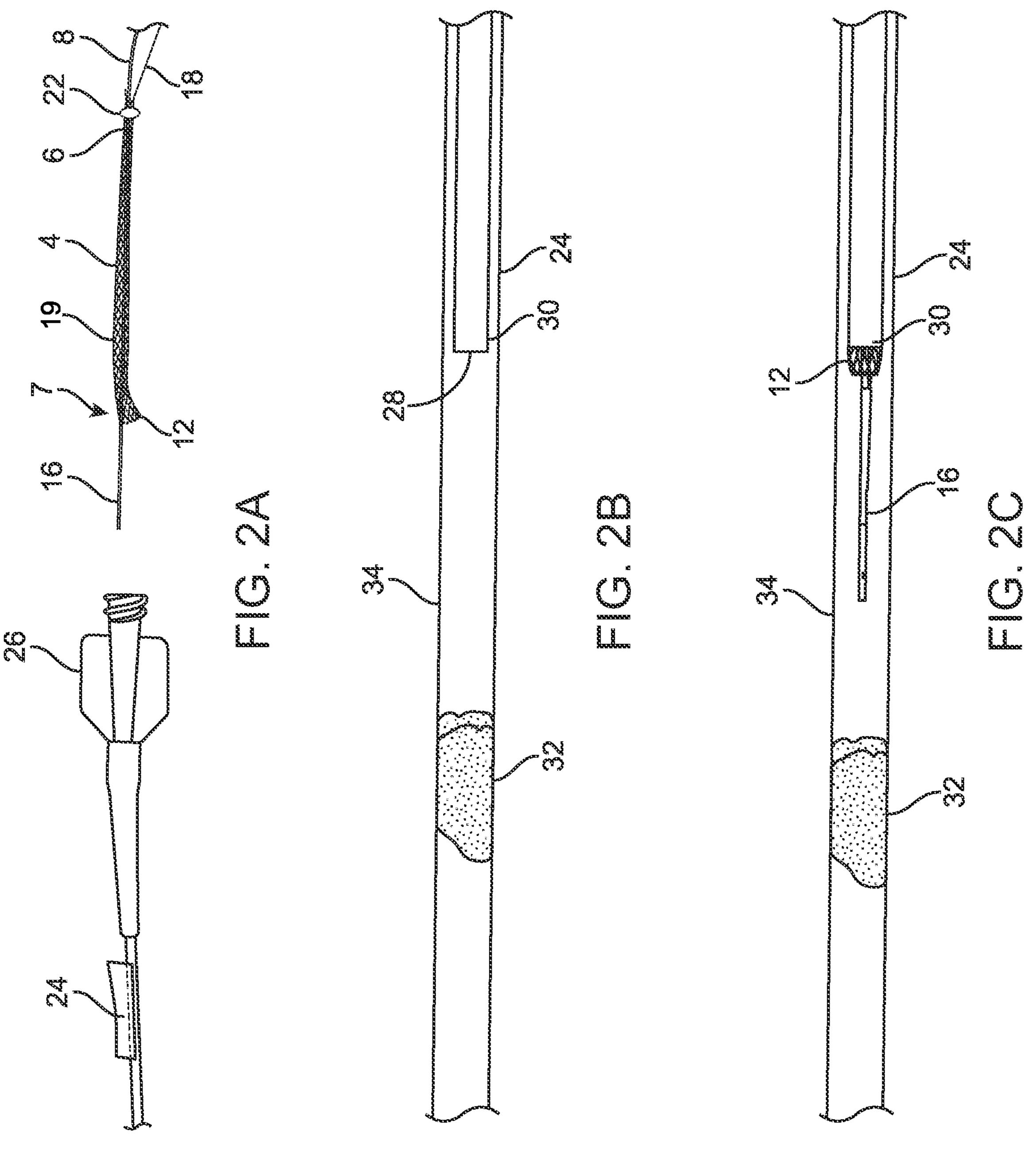
FIG. 2A illustrates the device of FIG. 1A with the containing element and a constraining catheter.
FIG. 2B illustrates the device of FIG. 1A with the constraining catheter positioned near a clot.
FIG. 2C illustrates the device of FIG. 1A with the distal opening of the containing element in a collapsed configuration in the constraining catheter.

In FIG. 2A, the proximal end of a constraining catheter 24 is shown with a constraining catheter luer 26. The containing element 4 can be inserted into the proximal end of the constraining catheter 24. In some embodiments, the containing element 4 is partially collapsed by moving the distal control body 8 in a distal direction to the bulk of the containing element 4 proximal control body 18. This applies an axial elongation force distally directed to the containing element 4 that causes it to both lengthen and also reduce in diameter as can be seen in the figure. More specifically, moving the distal control body 8 distally relative to the proximal control body 18 results in the distal control body 8 pulling the containing element 4 in a distal direction and additionally may contribute to the collapsing of the containing element 4 such that its diameter reduces and it can therefore be advanced more easily through a constraining catheter 24. An introducer sheath may be used to facilitate inserting the containing element 4 into the constraining catheter 24.

In FIG. 2B, the constraining catheter 24 has been navigated to a vessel 34 which includes a material to be removed, in this case an occlusive clot 32. This embodiment shows the size on scale with an application in ischemic stroke, but the device 2 may be scaled and sized appropriately for many other clinical uses. In the cerebral artery, for example, the vessel 34 may have an inner diameter from and including about 2 mm to and including about 4 mm and the clot 32 may have a length from and including about 4 mm to and including about 30 mm. The constraining catheter 24 has an inner lumen 28 and a distal end 30 that is positioned near the clot 32. In some embodiments, the containing element 4 is not inserted into the proximal end of the constraining catheter 24 until it is in position within the vessel 34 which allows the use of other components such as guidewires and microcatheters to aid in navigation to the vessel 34 before inserting the containing element 4. In other embodiments, the containing element 4 can be pre-loaded in the constraining catheter 24 anywhere along its length before navigation to the vessel 34.

In FIG. 2C, the containing element 4 has begun to be deployed out of the distal end 30 of the constraining catheter 24. It can be appreciated that while the containing element 4 is within the lumen 28, the constraining catheter 24 is at least partially collapsing or constraining the containing element 4. The containing element 4 may also be partially collapsed by the elongation applied to it by the distal control body 8. The distal control body 8 can be distally advanced to deliver and deploy the containing element 4 out of the constraining catheter 24. In some embodiments, the distal control body 8 can be held stationary while the constraining catheter 24 is withdrawn, which also deploys the containing element 4. Regardless, a distally directed force is imparted on the distal control body 8 to the containing element 4 that assists in translating the containing element 4 relative to the constraining catheter 24 and further may collapse the containing element 4 such that it can translate. In some embodiments, the extension tip 16 can be delivered past the clot 32 during deployment of the containing element 4.

Figure 2D:
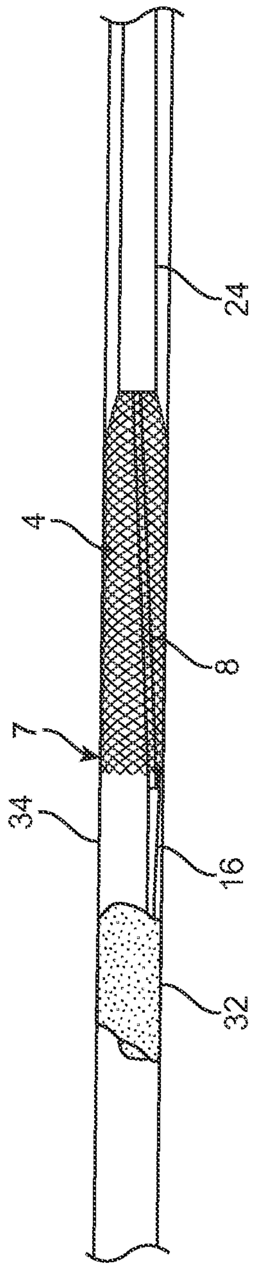
FIG. 2D illustrates the device of FIG. 1A with the containing element in an expanded configuration in the vessel.

In FIG. 2D, containing element 4 has been deployed and transitioned from a collapsed configuration to an expanded configuration within the vessel 34. The transition can be at least partly due to the distal control body 8 relaxing some or all of the distally directed force on the distal portion of the containing element 4. As the elongation tension on the containing element 4 reduces, it can expand towards the unbiased shape of the containing element 4. In some embodiments, a proximally directed force by the distal control body 8 on the containing element 4 can contribute to some or all of the expansion of the interior chamber 20. For example, if the containing element 4 is a braid construction a compressive force which is proximally directed can cause the braid to expand in diameter. The outward expansion of the interior chamber 20 can thus be pre-determined or controlled by the device 2 or by the user. The interior chamber 20 can be sized such that it provides intimal contact with the vessel wall and passively expands to the size of the vessel 34. In this figure, the distal control body 8 can be relaxed such that no tension or a reduced amount of tension is applied to the containing element 4, allowing it to expand towards its unbiased shape. At this point, the containing element 4 has a distal opening 7 which is facing the clot 32. The membrane 5 on the surface of the interior chamber 20 additionally provides flow arrest within the vessel. As can be seen, with the containing element 4 in an expanded configuration, the vessel 34 may be occluded and a membrane 5 on at least a portion of the containing element 4 may prevent the passage of blood flow. Accordingly, while implementations of the current disclosure are generally discussed in the context of removing material (e.g., clot 32) from a vessel, in at least some embodiments, the device 2 can alternatively or additionally be used primarily for blocking blood flow while simultaneously providing a working lumen through with other devices or fluids can be administered. This could include but not limited to glue type materials, liquid embolic agents, alcohol or sclerosing agents, in addition to chemotherapeutic agents. Varying the diameter and size of the flow arrest portion of membrane 5 will modify or arrest local vessel flow which can be useful during the controlled delivery or injection of these agents.

Figure 2E:
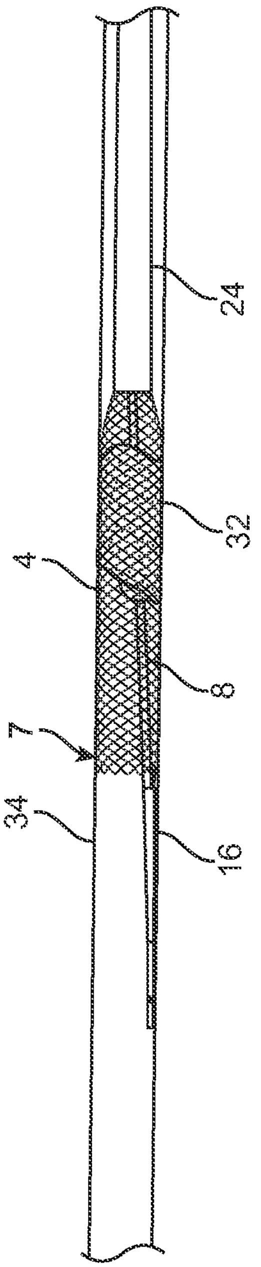
FIG. 2E illustrates the device of FIG. 1A with the clot withdrawn into the containing element.

In FIG. 2E, the clot 32 has been withdrawn into the interior chamber 20 of the containing element 4. In the embodiment shown, this can be accomplished by applying aspirational suction pressures to the proximal end of the constraining catheter 24. The aspiration path goes from a suction source, through the constraining catheter 24, into the proximal end of containing element catheter 6, through the interior chamber of containing element 4, and out the distal opening 7 into the vessel 34. Since the device 2 additionally restricts proximal blood flow, any suction comes distally from the device 2 and as such the clot 32 can be pulled into the containing element 4. In some embodiments, any number of other devices or methods may be used to bring the clot 32 into the interior chamber 20. For example, a stent retriever device may be used to physically grab the clot and pull it into the interior chamber 20. The stent retriever could be fully removed from the containing element and constraining catheter 24 leaving the clot 32 behind in the interior chamber 20. Alternatively, the stent retriever and clot 32 can both remain in the containing element 4. In some embodiments, the user may choose to use a combination of aspiration and stent retriever. In still other embodiments the interior chamber 20 may alternatively be advanced while the clot 32 is stationary to move it into the interior chamber 20.

Figure 2F:
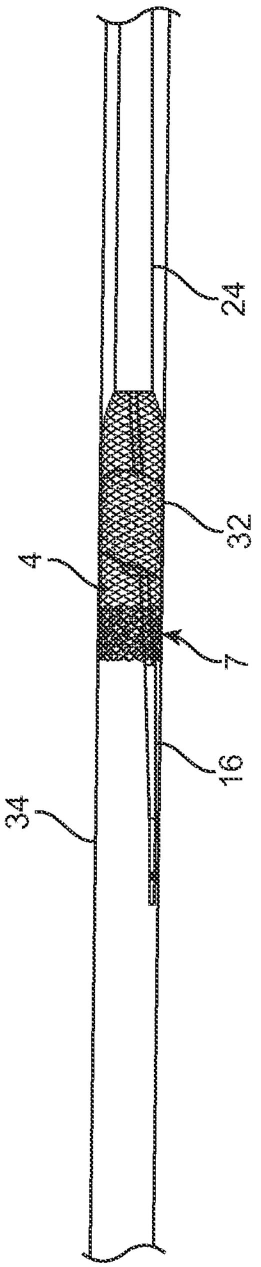
FIG. 2F illustrates the device of FIG. 1A with the containing element in a closed configuration.

In FIG. 2F, the distal opening 7 of the containing element 4 is restricted by withdrawing or otherwise applying a proximally directed force on the distal control body 8. This can cause the distal opening 7 of the containing element 4 to transition to a closed configuration which is shown in an inverted geometry. Alternatively, the distal opening 7 can simply bunch up and close. In an alternative embodiment, the distal control body 8 can instead be advanced distally to apply a distally directed force on the containing element 4 again and cause the containing element 4 to elongate and collapse around the clot 32. In this embodiment, the distal opening 7 also reduces in size as the diameter of the containing element 4 collapses similar to what is shown in FIG. 2A. In still other embodiments, the distal opening 7 can be closed through a purse-string mechanism where the filament 10 is pulled, creating a snare at the end that cinches the distal opening 7 and creates a closed configuration. The device 2 can now be withdrawn from the patient and the clot 32 is at least partially or fully contained by the containing element 4. In some embodiments, the entire device 2 including the constraining catheter 24 can be removed from the vessel 34. In other embodiments, the containing element 4 can be removed by pulling the proximal control body 18 while the constraining catheter 24 remains in situ within the vessel 34. This may allow the user to remove any clot 32 from the containing element 4 and then re-insert it into the constraining catheter 24 to withdraw additional material. This option may prove useful to the user by preserving access and purchase to the occluded vessel.

The closure of the distal portion can be reversed such that the user can control whether the distal opening 7 is open or closed by controlling and manipulating the distal control body 8. In some procedures, after closing the distal opening 7 the user may use additional tools to remove the clot 32 before removing the device 2 from the patient. For example, a spinning or translating morcellating tool with or without aspiration may be used to break up the clot 32 and remove the clot 32 through the lumen of the containing element catheter 6. With the clot 32 completely encased within the containing element and excluded from the vessel lumen clot 32 maceration would potentially be more efficacious and avoid inadvertent vessel wall injury by mechanical clot disruption within the enclosed containing element. An additional possible advantage to such an embodiment is that the clot 32 can be fully removed from the patient through the lumen of the device 2 with the distal opening 7 closed, and then the distal opening 7 can be opened again and additional attempts at clot 32 removal can be completed. This is particularly advantageous when the clot 32 breaks apart and only a fraction of the clot 32 comes into the containing element. In such a scenario it may be advantageous to remove the fraction of clot 32 without removing the device 2 from the patient and then simply opening the distal opening 7 again and capturing the remaining clot 32.

Figure 3:
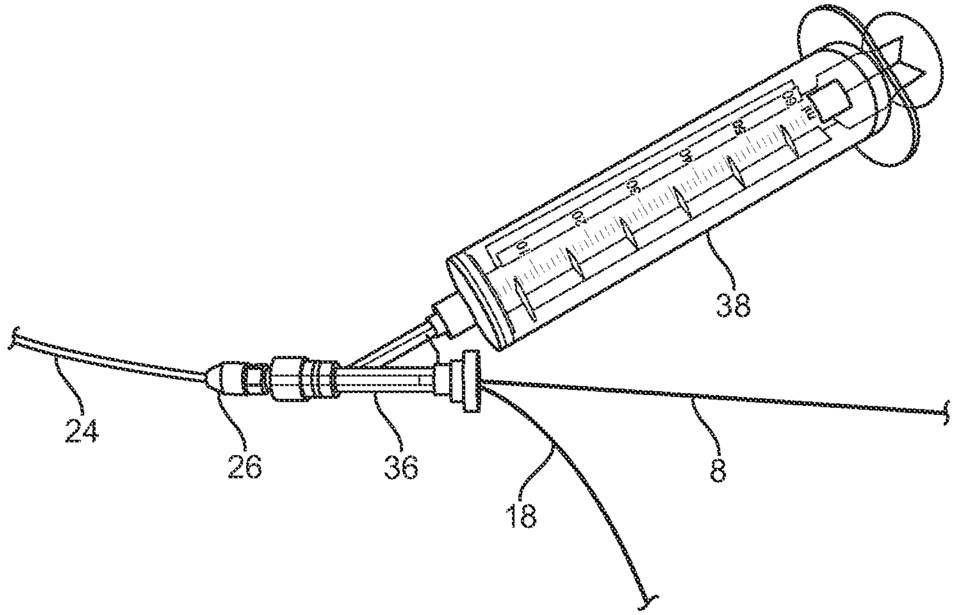
FIG. 3 illustrates a suction source for use with the device of FIG. 1A.

In FIG. 3, the proximal end of the constraining catheter 24 is connected to a hemostasis valve 36 which allows connection to a suction source 38. The suction source 38 shown is a large syringe for generating aspiration but any number of other devices such as vacuum pumps are contemplated. As can be seen, the aspiration path would flow from the suction source 38, through the hemostasis valve 36, through the constraining catheter 24, then through the containing element 4, and finally into vessel 34. The distal control body 8 and proximal control body 18, and any number of other components such as guidewires and microcatheters, can pass through the hemostasis valve 36 providing the user with control of the containing element 4. By advancing the distal control body 8 and keeping the proximal control body 18 stationary, the containing element 4 elongates. By withdrawing the distal control body 8, the containing element 4 expands and then eventually closes at the distal opening 7. And by withdrawing the proximal control body 18, the containing element 4 is withdrawn into the constraining catheter 24. A handle mechanism is contemplated that could be attached to the hemostasis valve 36 and allow control of the distal control body 8 and the proximal control body 18 through interfaces such as sliders, triggers, or knobs. The proximal end of the containing element catheter 6 may include a handle that allows for simple manipulation and control by the user. The handle may include visual indicators or other sensory feedback to alert the user what configuration device 2 is in at a given moment. For example, the distal control body 8 could be connected to a slider that allows distally or proximally directed forces and its axial position relative to the containing element 4 and proximal control body 18 to be controlled and locked in place which controls the shape of the containing element 4. Any number of mechanisms within the handle may be contemplated such as ratchet mechanisms, geared mechanisms, friction brake mechanisms, spring mechanisms, motorize mechanisms, or any other suitable mechanism. During navigation through the constraining catheter 24, the distal control body 8 can be extended to elongate the containing element 4 and thereby decrease its diameter to facilitate delivery. Once the containing element 4 is deployed out of the constraining catheter 24, the distal control body 8 can be withdrawn to allows the containing element 4 to transition into an expanded configuration that includes an expanded distal opening 7. Once a part of the clot 32 is withdrawn into the interior chamber 20, the containing element 4 can transition to a closed configuration by either withdrawing the distal control body 8 to invert the distal portion, or extending the distal control body 8 to collapse the containing element 4. Using a handle to control the motion of the distal control body 8 and proximal control body 18 may improve user interface. Additionally, in some embodiments, the rotation of distal control body 8 and/or proximal control body 18 can be controlled. For example, the distal control body 8 can be rotated to improve navigation during delivery or to transition the containing element 4 into a closed configuration.

The device 2 shown in FIG. 1 will now be described in more detail including its materials and construction. The containing element 4 may be made partly of a metallic or polymer structure with or without a membrane 5 externally. The structure can be a braid or a scaffold and can be formed with any number of elements. The containing element 4 can have an interior chamber 20 formed by an outer wall 19 portion. In some embodiments, the containing element is a braid formed of a metal such as Nitinol, stainless steel, titanium or any other suitable material. The wire used for the braid construction may be on the order of from and including about 5 um to and including about 200 um or from and including about 12 um to and including about 100 um or about 50 um in diameter. The braid can have a braid angle from and including about 80 degrees to and including about 160 degrees or from and including about 100 degrees to and including about 140 degrees or about 120 degrees. In the case where the braid is formed of Nitinol wire, the braid can be shaped into any number of shapes either during the braid process or using shape setting and shape memory processes. In other embodiments, the containing element 4 can be made partly of a scaffold that is formed by laser cutting or chemical etching or any other suitable process. For example, the outer wall 19 portion can be manufactured by laser cutting a Nitinol tube or a rolled flat sheet into a pattern that is capable of collapsing and expanding, like a stent. The containing element 4 can have any number of different profiles and sections. In some embodiments, the containing element 4 has a single diameter that is roughly the size or larger than the target vessel 34. For example, for neuro thrombectomy procedures where a clot 32 is being removed from the middle cerebral artery (MCA), the containing element can have a nominal unconstrained or unbiased diameter from and including about 1.0 mm to and including about 8.0 mm or from and including about 2.0 mm to and including about 6.0 mm or about 5 mm. In other embodiments, the containing element 4 may have a flared-outward distal opening 7 that further ensures that the containing element is fully opened at the distal opening 7 when it is deployed. In other embodiments, the containing element 4 may have a flared-inward distal opening 7. In some embodiments, the containing element 4 may transition to smaller diameters where it connects to the containing element catheter 6 and may roughly match the containing element catheter 6 size. In this example, the containing element 4 may have tapered or funnel area where it transitions from a larger diameter to a smaller diameter. The size of the different areas and taper may be formed by shape setting or braiding or any other suitable method. In some embodiments, the containing element 4 is manufactured as a single diameter and the proximal end is constrained onto the containing element catheter 6 during manufacturing to create a taper from the larger diameter to the smaller diameter. This can be done with heat shrink, reflow of plastic, laser welding, or any other suitable technique.

The containing element 4 can have an overall length suited to its procedure. In embodiments where the containing element 4 is used primarily to restrict blood flow, the containing element 4 can be shorter and may only need to be long enough to ensure that it adequately opposes the vessel walls or provides a funnel for clot removal. In embodiments such as any thrombectomy where a clot is being extracted, the containing element 4 may be sized to receive the clot and any additional elements such as graspers or stent retrievers. For example, the containing element 4 may have a length from and including about 5 mm to and including about 100 mm or from and including about 20 mm to and including about 60 mm or about 35 mm. In some embodiments, the containing element 4 can be relatively short and only provide flow arrest for an aspiration procedure with minimal clot containment. In other embodiments, the containing element 4 can be longer to contain a clot 32 with or without a stent retriever.

The outer wall 19 portion of the containing element 4 can include a membrane 5 that covers open areas between the structure of the containing element 4 to restrict blood flow or assist in the opening and closing of the device 2. The membrane 5 can be made of silicone, polyurethane, Pebax, elastomer, or any other suitable material. The membrane 5 can stretch to allow the containing element 4 to expand and constrict as described herein. The membrane can be from and including about 1 um to and including about 200 um or from and including about 5 um to and including about 50 um or about 10 um. The membrane 5 can be applied through dip coating or spray coating processing and adhered to the structure or additionally bonded with thermal processes or chemical curing processes. In some embodiments, the braid or structure can be placed on a mandrel and dipped to apply the membrane 5 on the outside surface of the braid. In an alternative embodiment, the braid can be placed in a tube and then dipped to apply the membrane 5 on the inner surface of the structure. In still other embodiments, a polymeric material can be laminated on the inner surface of the structure using heat to create a membrane 5. In these embodiments, the braid wires directly contact the inner lumen 28 of the constraining catheter 24 and thereby have potentially lower friction than if the membrane 5 is on the outer surface and contacts the inner lumen 28.

In some embodiments, the membrane 5 exists over the entire length of the interior chamber 20, from the distal opening 7 to the containing element catheter 6 and contains the clot 32 during retrieval. In other embodiments, the membrane 5 only exist over a portion of the interior chamber 20 from and including about 1% to and including about 90% of the length or from and including about 10% to and including about 80% of the length or about 50% of the length. In some embodiments, the membrane 5 does not cover a some of the distal portion. In other embodiments, the membrane 5 may only exist over a proximal portion where the containing element 4 tapers into the constraining catheter 24. Therefore, the membrane 5 can restrict or fully arrest blood flow at the tapered region even though the entire interior chamber 20 portion is not covered by the membrane 5.

The base membrane 5 can include any number of additional coating layers such as lubricious coatings to reduce friction such as hydrophobic coatings, hydrophilic coatings, silane, surface treatments, plasma vapor depositions, or any other suitable outer layer for friction reduction. The coating may further include drug eluting coatings to deliver therapeutic agents or radiopaque elements such as barium sulfate within its material composition.

In some embodiments, the flow restriction achieved by the containing element 4 does not need to be binary, meaning on or off. The flow restriction can be attenuated and controlled to achieve a desired flow rate, pressure, or blood supply. In such embodiments, the device 2 can include a set of mechanisms that control the opening of the containing element 4 using the distal control body 8 motion. Electronic and control algorithms can be applied to achieve a user target for blood flow. This can be controlled manually by the user or can be done automatically such that a processer determines what the desired target is and then determines the appropriate amount of opening of the containing element 4 and movement of the distal control body 8. In still other embodiments, the containing element 4 can be opened automatically by a processer depending on the step of the procedure. For example, in certain steps of the procedure it may be desirable to have more or less flow than other steps. Blood flow is important for brain health and although an ischemic stroke generally decreases blood flow, restoring blood flow quickly is imperative. The device 2 may automatically restore blood flow at given intervals rather than only restoring blood flow after the clot is fully contained. Variable flow arrest may additionally be advantageous during controlled endovascular embolization or sclerosant treatment of high flow arterio-venous malformations or fistulas. Additionally, the user-controlled re-establishment of flow may be used to gradually restore flow and therefore prevent reperfusion injury. For example, after a clot has been removed the containing element 4 can be collapsed over a duration of time that allows gradual reperfusion of the ischemic tissue.

Taken together, the structural elements of the containing element 4, in some embodiments a braid, and the membrane 5 create an expandable interior chamber 20 formed by the outer wall 19. The containing element 4 has an unbiased diameter that can be collapsed for delivery through the constraining catheter 24 or through the patient's vasculature. When the containing element 4 is within a vessel 34 that is at least partially smaller than the outer diameter of the containing element 4, it can apply an outward expansion pressure on the vessel 34. The outward expansion pressure can be considered the radial force or pressure that maintains the patency of the containing element 4. The outward expansion pressure can be designed and predetermined such that a vacuum pressure within the interior chamber 20 that is used to aspirate the clot 32 does not significantly collapse the interior chamber 20. In physics, a perfect vacuum has a pressure of about 760 mmHg, so an outward expansion pressure above this number plus any blood pressure on the outer surface would ensure that the interior chamber 20 would not collapse under the pressures of aspiration on the inner surface and blood pressure on the outer surface. During delivery through a constraining catheter 24, the outward expansion pressure creates frictional drag between the containing element 4 and the inner lumen 28, especially through tortuous curvature. Therefore, a lower outward expansion pressure of the containing element 4 would in theory reduce the force required to translate the containing element 4 through the constraining catheter 24. Additionally, by applying a distally directed force at the distal portion of the containing element 4 can reduce the outward expansion pressure during delivery. In some embodiments, the outward expansion pressure is at least about 300 mmHg to about and including 2000 mmHg or from about 600 mmHg to and including about 1200 mmHg or about 900 mmHg. The outward expansion pressure can be adjusted by the construction of the braid including wire diameters, wire count, material type, etc., and by the membrane 5 material and thickness.

The containing element catheter 6 may be constructed using catheter manufacturing techniques. This may include using braids, coils and tubes to control flexibility and stiffness of the catheter along its length. Plastics such as Pebax or others may be used to laminate and similarly control the flexibility along the length. Lubricious jackets and inner sleeves as well as hydrophilic coatings may be used to lower the friction of the containing element catheter 6 along any portion. In other embodiments, the containing element catheter 6 may simply be considered a reduced diameter portion of the containing element 4 braid and/or membrane 5, and does not include a separate catheter construction. In these embodiments, the containing element catheter 6 can either be not expandable or less expandable than the interior chamber 20 portion of the containing element 4. The containing element catheter 6 may be sized appropriately for its application. For neurovascular applications such as thrombectomy procedures, the containing element catheter 6 may have an outer diameter from and including about 0.5 mm to and including about 3.0 mm or from and including about 1.0 mm to and including about 2.0 mm or about 1.6 mm.

In some embodiments, the containing element catheter 6 is relatively short on the order from and including about 0.1 cm to and including about 20 cm or from and including about 0.5 cm to and including about—10 cm or about 1 cm long. In this case, the proximal end of the containing element catheter 6 terminates within the inner lumen 28 of the constraining catheter 24. As discussed in more detail below, the aspiration path therefore flows through the inner lumen 28 of the constraining catheter 24 first before entering the containing element catheter 6 and the interior chamber 20. In other embodiments, the containing element catheter 6 can be longer, from and including about 40 cm to and including about 200 cm such that it extends out of the constraining catheter 24. In these embodiments, the suction source can be applied directly to the containing element catheter 6 and the aspiration path does not flow through the inner lumen 28 of the constraining catheter 24. In either case, the force exerted on the clot 32 by the aspiration from the expandable interior chamber 20 of containing element 4 is higher than if the aspiration came only from the distal end 30 of constraining catheter 24.

The containing element catheter 6 or outer wall 19 portion of the containing element 4 may include a sealing surface 22 on its outer surface. The sealing surface 22 creates an effective seal between the containing element 4 and the inner lumen 28 of the constraining catheter 24. This enables suction that is applied to the proximal end of constraining catheter 24 to flow through the lumen of containing element 4 and not leak significantly from the distal end 30 of the constraining catheter 24. The sealing surface 22 may be a round O-ring type interface that extends radially on the containing element catheter 6 and compresses slightly against the inner lumen 28. In other embodiments, the sealing surface 22 may be like a lip seal with one or more sealing surfaces that interface with the inner lumen 28. In still other embodiments, the inner lumen 28 may contain a sealing surface such as a narrowed or tapered profile which provides an effective seal by axially sliding the containing element catheter 6 into the constraining catheter 24 so that the outer surface of the containing element catheter 6 wedges against the inner lumen 28. The outer surface of containing element catheter 6 may additionally have a tapered region for sealing against a portion of the inner lumen 28. The sealing surface 22 may create a significant seal that is full or partial between the containing element 4 and the constraining catheter 24 when exposed to vacuum from and including about 10 mmHg to and including about 760 mmHg.

As shown, a proximal control body 18 may be added to the proximal end of the containing element 4 such that the containing element 4 can be pulled and/or pushed at its proximal end. The proximal control body 18 can be any number of elements including wires, tubes or other constructions. In some embodiments, the proximal control body 18 can run coaxially inside or outside of the distal control body 8. The distal control body 8 can therefore advance the containing element 4 forward by pulling the containing element 4 from its distal end and the proximal control body 18 can retract the containing element 4 proximally by pulling the containing element 4 from its proximal end. The distal control body 8 and proximal control body 18 can therefore also change the shape of the containing element 4 by elongating it or compressing it. In some embodiments, the proximal control body 18 is simply the elongated containing element catheter 6 which allows for positional control of the proximal end of the containing element 4.

The distal control body 8 connects to the distal portion of the containing element 4 and may extend through the interior chamber 20 and through the entire containing element catheter 6 such that the user has access to the distal control body 8. For neurovascular applications, the distal control body 8 may be an outer diameter from and including about 0.1 mm to and including about 1.0 mm or from and including about 0.2 mm to and including about 0.6 mm or about 0.38 mm. In some embodiments the distal control body 8 may be similar in construction to existing guidewires that has sufficient flexibility to navigate through the constraining catheter 24 but sufficiently strong to control the distal opening 7 of the containing element 4. For example, the distal control body 8 may be made partly of a thin-walled tube that is cut for enhanced flexibility or a tight wound coil or a composite of such structures. It may include a core wire that is tapered to alter the flexibility and stiffness along the length of the distal control body 8. The distal control body 8 materials may be Nitinol, stainless steel, Pebax, or any other suitable material. In other embodiments, the distal control body 8 may be a composite of multiple materials similar to a microcatheter with braided or coiled elements laminated with plastic. The distal control body 8 may additionally have lubricious coatings applied on any of its surfaces including the outer diameter or inner diameter. The distal control body 8 may be relatively straight and uniform profile along its length or may include any number of bends or profile changes along its length. In an alternate embodiment where the containing element catheter 6 is longer, the distal control body 8 may exit the containing element catheter 6 through a hole such that the distal control body 8 is outside the inner lumen 28 similar to a Rapid Exchange design which may provide more internal lumen space within the containing element catheter 6 and obviate the need for an exchange length guidewire. This may be advantageous if the containing element catheter 6 is to be placed over a pre-deployed stent retriever via a Rapid Exchange technique for rapid clot extraction. In still other embodiments, the distal control body 8 may be entirely outside of the containing element catheter 6 and containing element 4 lumen and may instead run externally along the outside of these components such that it does not take up any additional space within them. This may allow for improved aspiration and placement of other devices within a smaller containing element catheter 6.

The distal control body 8 can move relative to the containing element 4 or proximal control body 18 which can apply forces to the distal portion of the containing element 4 and can then transition the containing element 4 through different configurations. In some embodiments, the distal control body 8 can apply a distally directed force to the distal portion of the containing element 4 by translating the distal control body 8 away from the containing element 4 during delivery that elongates and collapses the containing element 4. When the containing element 4 is within a constraining catheter 24, the expandable interior chamber 20 applies an outward expansion pressure towards its unbiased shape. For example, if the constraining catheter 24 inner lumen 28 is about 1.2 mm in diameter and the unbiased diameter of the containing element 4 is about 5 mm in diameter, then when the containing element 4 is within the inner lumen 28 it applies an outward expansion pressure. Pushing the containing element 4 through the constraining catheter 24 from the proximal end will cause it to try and expand further and therefore increase the outward expansion pressure making it harder to advance through the constraining catheter 24. However, by applying a distally directed force at the distal portion, for instance with the distal control body 8, will cause the outward expansion pressure to instead decrease. The containing element 4 may or may not collapse further within the inner lumen 28, but the outward expansion pressure will decrease and therefore make advancement through the constraining catheter 24 easier.

During expansion, the distal control body 8 can also cause the containing element 4 to expand by either reducing the distally directed force and allowing the containing element 4 to return to a larger unbiased shape, or by applying a proximally directed force that actively causes the containing element 4 to expand by applying a compressive load. During closure, the distal control body 8 can apply a proximally directed force to the distal end of the containing element 4 by translating the distal control body 8 proximally and which transitions the containing element 4 to a closed configuration. Alternatively, the distal control body 8 can transition the containing element 4 to a closed configuration by collapsing the containing element 4 with a distally directed force. The proximal control body 18 can similarly apply forces to the proximal portion of the containing element 4. In some embodiments, the proximal control body 18 applies a distally directed force on the proximal end of the containing element 4 during delivery to assist in the translation of the containing element 4 through the constraining catheter 24. The proximal control body 18 can also apply a proximally directed force on the proximal end to move the containing element 4 proximally for positioning, during withdrawal from the patient, or to move the containing element 4 proximally into the constraining catheter 24. It should be appreciated that any number of these force applications of the distal control body 8 and proximal control body 18 are contemplated. For example, the proximal control body 18 can be a thin wire that does not apply distally directed pushing during delivery. In such an embodiment, the containing element 4 may elongate and collapse due to the distally directed pulling of the distal control body 8 and the friction within the inner lumen 28. Similarly, the distal control body 8 can be a thin wire that does not apply distally directed force during delivery and is only used to close the distal opening 7. In one embodiment, the distal control body 8 and the proximal control body 18 apply distally direct forces during translation of the containing element 4 through the constraining catheter 24 and translate together. The containing element 4 is held in an elongated and collapsed configuration during the delivery. Once at the target vessel, the distally directed force on the proximal control body 18 is reduced followed by a reduction in the distally directed force on the distal control body 8. The containing element 4 then transitions to an expanded configuration within the vessel 34 providing blood flow arrest. After the procedure, a distally directed force is applied to the containing element 4 by translating the distal control body 8 relative to the containing element 4 and which transitions the containing element 4 to a collapsed configuration. A proximally directed force is then applied to the proximal control body 18 and the DBC 8 to remove the containing element 4 through the constraining catheter 24.

The loops 12 on the distal control body 8 are shown as an atraumatic braid termination where the braid wires are wound back on themselves. This creates a series of rounded ends and a location to attach the distal control body 8. In other embodiments, the loops 12 could be elsewhere along the length of the containing element 4 and not necessarily at the distal opening 7. For example, the loops 12 could be considered any portion of the containing element 4 that the filament 10 can attach to. In other embodiments, the loops 12 could be other shapes such as eyelets or hooks. In still other embodiments where the containing element 4 is not a braid, the loops 12 could be any attachment point along the length of a laser cut tube such as a hole or laser weld.

The filament 10 may be woven through one or more loops 12 attached to the distal control body 8 through one or more filament connections 14. As shown in FIG. 1, the filament 10 is a round wire that weaves through 1-4 of the loops 12 at the end of the containing element 4. In this embodiment, the filament 10 does not approximate the perimeter of the distal opening 7 of containing element 4 and when the clot 32 is withdrawn into the interior chamber 20, it does not pass through the filament 10. This may be beneficial since the target vessels 34, in the case of the MCA for instance, may vary in diameter from and including about 2 mm to and including about 5 mm. While the braid is capable of expanding and contracting to match the diameter of the vessel 34, a filament 10 that circumferentially goes around the end of the containing element 4 may be limited in its ability to expand and contract. This may create situations where the filament 10 obstructs the distal opening 7 to the containing element 4. By tacking the distal control body 8 at only 1-3 loops on single side of the containing element, the filament 10 does not need to expand to match the diameter of the vessel 34 and instead remains at the side of the distal opening 7. This allows the braid to expand to the vessel size and geometry. The filament 10 is then attached to the distal control body 8 such that the forward movement of the distal control body 8 elongates the containing element 4. The filament 10 does not necessarily need to extend forward of the distal opening 7 and can instead both weave through the loops 12 and be attached to the distal control body 8 at locations that are proximal to the distal opening 7.

An extension tip 16 may exist as a part of the distal control body 8 at its distal most end. The extension tip 16 may extend beyond the filament connection 14 and provide trackability and navigation for the user. The extension tip 16 may be made of similar materials and manufacturing methods as guidewires such as coils, laser cut tubes, and tapered core wires made partly of Nitinol, stainless steel, and plastic. The extension tip 16 may include a stiffness transition region from flexible at the tip to stiffer at the filament connection 14. This allows the extension tip 16 to navigate through the constraining catheter 24 or through vessels 34 with tight tortuosity yet provide sufficient stiffness to elongate the containing element 4. In some embodiments, the extension tip 16 may be formed from the same material as the distal control body 8. In the case of neuro thrombectomy, the extension tip 16 may be from and including about 0.1 to and including about 5 cm long or from and including about 0.5 cm to and including about 2 cm long or about 1 cm long. The extension tip 16 may also be removable from the distal control body 8 such that the user can decide whether to use the extension tip 16 or not. In some embodiments, the extension tip 16 may have any number of bends or profiles to assist with navigation or clot retrieval from and including about 0 degrees to and including about 135 degrees bends, curls, or any other suitable profile. In some embodiments, the extension tip 16 can be malleable and can be shaped by the user prior to surgery into a desired predetermined shape. In some embodiments, the extension tip 16 may be rotationally independent from the distal control body 8. In some embodiments, the distal control body 8 does not have an extension tip 16 and does not extend beyond the distal end of the containing element 4. The distal control body 8 can simply connect to a distal portion of the containing element 4 without extending beyond the distal opening 7. In some embodiments, the extension tip 16 may include clot engagement features that disrupt the clot 32 to assist in its movement during aspiration.

The device 2 may additionally have radiopaque characteristics such that it is visible using fluoroscopy. This may include the use of radiopaque material such as platinum, tungsten, gold or any other suitable material. For example, the filament 10, extension tip 16, distal control body 8, proximal control body 18 may be made partly of radiopaque materials. Similarly, the wire used in the braid of the containing element 4 may made partly of Nitinol with a platinum core. Marker bands or other radiopaque components may also be secure to the device 2 so that the location of the device 2 can be ascertained by the user.

Lubricious or low friction coatings may additionally be employed in any component within device 2. For example, the containing element catheter 6 may include a hydrophilic coating on the outer surface and PTFE jacket on the inner lumen. Other components such as the distal control body 8 may also have lubricious coatings that enable the device 2 to work as intended through tortuous vasculature.

Figure 4:
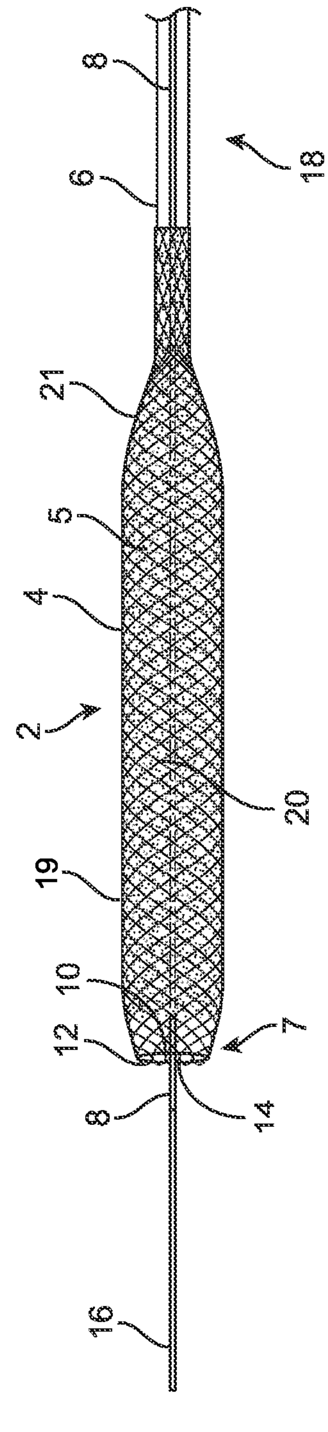
FIG. 4 illustrates an alternative embodiment of a device according to the present disclosure in an expanded configuration

In FIG. 4, an embodiment of the device 2 is shown. The device 2 includes a containing element 4 connected to a containing element catheter 6 and a distal control body 8. In this embodiment, the containing element catheter 6 can extend through the entire length of the constraining catheter 24 such that the containing element catheter 6 becomes a proximal control body 18 capable of moving the proximal end of containing element 4. The containing element 4 includes a membrane 5 that covers the interior chamber 20 and extends near to the distal opening 7 of the containing element 4. At the distal opening 7 of the containing element 4, a filament 10 is woven through one or more loops 12 and attached to the distal control body 8 at a filament connection 14. The filament 10 in this embodiment approximates the perimeter of the containing element 4. A constraining catheter 24 is not shown in FIGS. 4-7 for clarity, but it should be appreciated that the device 2 could include a constraining catheter 24 and the elongated containing element 4 could be used with or without a constraining catheter 24.

The filament 10 can be a round wire of a constant diameter from and including about 5 um to and including about 300 um or from and including about 50 um to and including about 150 um or about 100 um. Alternatively, the diameter of the wire can vary along the length of the filament 10 and can be larger in some areas and smaller in others which may allow variable stiffness and flexibility of the filament 10 at various points which may beneficially allow the wire to bend preferentially in certain areas. In other embodiments, the filament 10 can be of other shapes and constructions than a round wire. The filament 10 shown in FIG. 2B is a generally circular shape. The circular diameter of the filament 10 may be any given size that is suited for its application. For example, for use within blood vessels the diameter may be from and including about 1 mm to and including about 50 mm depending on the vessel. For cerebral arteries the diameter may be from and including about 2 mm to and including about 6 mm or from and including about 3 mm to and including about 5 mm. The shape of the filament 10 may be determined by the natural curvature of the filament 10 as it connects to the distal control body 8. Alternatively, the shape of filament 10 may be at least partially predetermined by other means such as plastic deformation, shape setting of Nitinol, mechanical properties and relative stiffnesses of a composite of materials, or any other means. The profile of the filament 10 can be generally circular with a diameter that generally matches the intended vessel diameter or slightly larger or slightly smaller than the vessel diameter. The profile can alternatively be non-circular and include any number of other shapes or features. The filament 10 can be made partly of metals such as Nitinol, stainless steel, or the like. Alternatively, filament 10 can be made partly of plastics such as suture, polyester, or the like.

In some embodiments, the filament 10 can be larger than the distal opening 7 of the containing element 4. In other embodiments, the user can adjust the size of the distal opening 7 before or during the procedure. For example, the size and shape of the filament 10 perimeter can be adjusted by pulling the filament 10 in or out of the distal control body 8. By adjusting the filament 10 shape, the device 2 can accommodate different vessel sizes and ensure that the distal opening 7 is fully opposed to the vessel wall while the clot is withdrawn into the interior chamber 20. Alternatively, the distal opening 7 can be actively transitioned to a collapsed or expanded configuration by the user during navigation, delivery, and removal.

The filament 10 can extend out of the distal control body 8 through one or more holes in the distal control body 8 at the filament connection 14. In this embodiment the distal control body 8 is a tube and the holes can be laser cut or otherwise added to the tube. The holes allow the filament 10 to enter and exit the distal control body 8 such that the profile of the filament 10 is generally at an angle from and including about 25 degrees to and including about 155 degrees or from and including about 60 degrees to and including about 120 degrees or about 90 degrees to the central axis of the distal control body 8. The filament 10 can run through the entire distal control body 8 and to the proximal end or alternatively it can terminate at any point within the distal control body 8. The filament 10 can be connected to the distal control body 8 by mechanical swaging, adhesives, laser welding, heat shrink, or any other suitable process. In other embodiments, the filament 10 can be an integral part of the distal control body 8 or vice versa. For example, the filament 10 could be formed by pieces of the distal control body 8 that are wrapped around into the looped profile or by pieces of the containing element 4 construction. In other embodiments, the distal control body 8 may simply be a continuation of the filament 10 ends that extend through the containing element 4 and containing element catheter 6. In such an embodiment, the filament 10 ends may be connected to keep them controlled within the lumen of the containing element catheter 6 lumen 2. In other embodiments, the filament 10 ends may connect together and one may terminate while the other filament end extends through the entire lumen of the containing element catheter 6.

In some embodiments, the filament 10 can be fixedly connected to the distal control body 8 such that movement of the distal control body 8 moves the filament connection 14 and thereby pulls the filament 10. In other embodiments, the filament 10 can move relative to the distal control body 8. When the clot is in the containing element 4 and the user wishes to transition to a closed configuration, they can pull the filament 10 relative to the distal control body 8 such that the profile of the filament 10 which was previously an open loop cinches like a purse string and closes. This can be a method of closing the distal opening 7 of the containing element 4.

The filament 10 may weave through all of the loops 12 or only a portion of the loops 12. In some embodiments, the filament 10 only weaves through from and including about 1 loop to and including about 128 loops or from and including about 2 loops to and including about 24 loops or about 4 loops. For example, the filament 10 may weave through a single loop 12 that is approximately on the opposite side of the perimeter of the distal opening 7 from the filament connection 14.

In some embodiments, the filament 10 may form part or all of the extension tip 16. For example, the extension tip 16 may be a coil or laser cut tube formed from the distal control body 8 and the ends of the filament 10 may be located coaxially within the extension tip to provide additional stiffness or flexibility in given areas.

The movements of the device 2 through various configurations will now be discussed. In FIG. 4, the device 2 is in a generally unbiased expanded configuration meaning the device 2 is not significantly radially constrained. In this configuration, the distal control body 8 is in a neutral unbiased position and does not have significant tension, compression, or rotational forces applied to it by the user. As can be seen, the filament 10 has a circular shape that is slightly smaller than the shape of the containing element 4 so that it is a slightly constricted at the distal opening 7 compared to the rest of its length.

Figure 5:
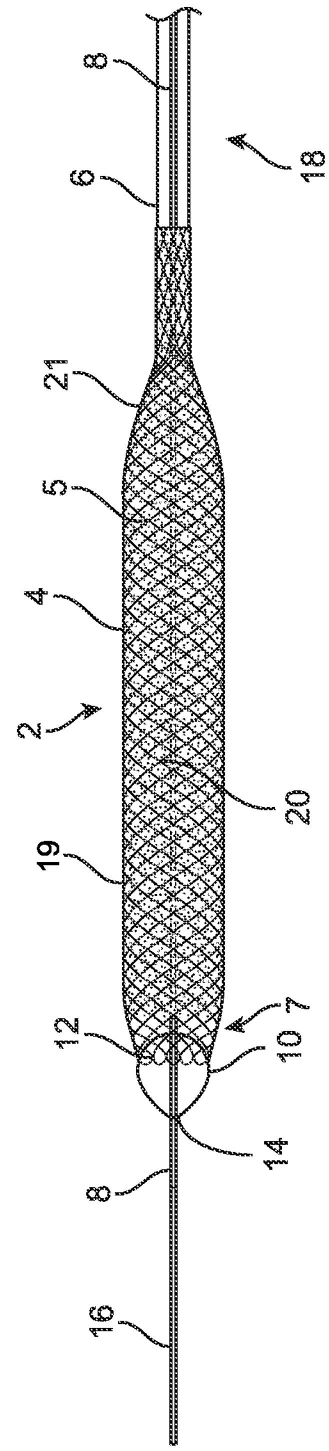
FIG. 5 illustrates the device of FIG. 4 transitioning to a collapsed shape

In FIG. 5, the device 2 is shown with a slightly collapsed or constricted shape. The distal control body 8 has moved distally relative to the containing element 4 and containing element catheter 6, and has therefore applied a distally directed force on the distal portion of the containing element 4 such it elongates and collapses. The user can push or otherwise translate the distal control body 8 out of the containing element catheter 6 from the proximal end of the device 2. Alternatively, the user can retract the containing element catheter 6 while holding the distal control body 8 stationary or any combination thereof. As the distal control body 8 moves relative to the containing element catheter 6, the filament connection 14 also moves and thereby pulls part of the filament 10 distally while the areas that are woven through the loops 12 remain further proximal. In this way, a distally directed force is applied to the containing element 4 since its proximal end is held by the containing element catheter 6 while its distal opening 7 is urged distally by the loops 12 that are woven by the filament 10. As the containing element 4 is placed in tension by the distally directed force, it begins to elongate and also constrict or otherwise reduce its diameter at least in some portions. In some embodiments, the device 2 may include a constraining catheter 24 which the sliding containing element 4 assembly can be inserted through. In this instance, the containing element 4 may already by collapsed by the inner lumen 28 such that the application of a distally directed force does not necessarily collapse the containing element 4. Instead, the distally directed force may simply decrease the outward expansion pressure of the containing element 4 and thereby reduce the force required to translate the containing element 4 through and out of the constraining catheter 24.

Figure 6:
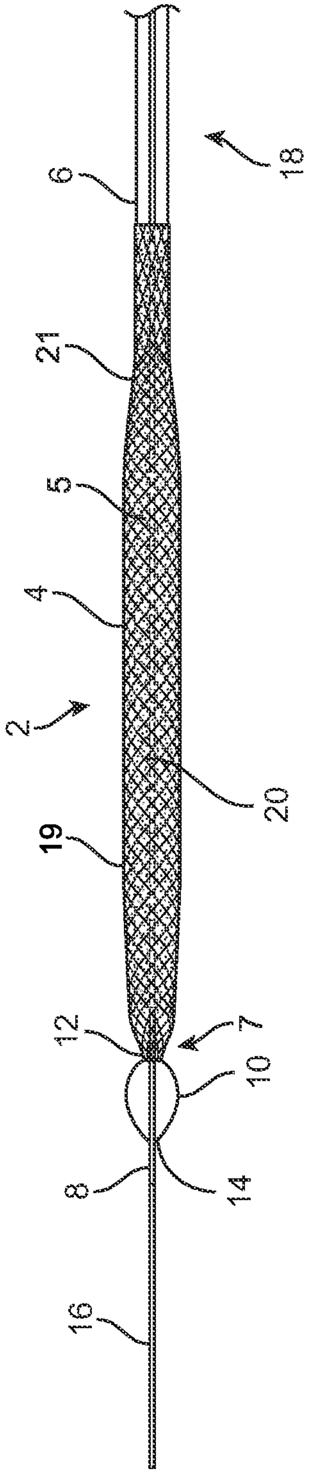
FIG. 6 illustrates the device of FIG. 4 further transitioning to a collapsed shape

In FIG. 6, the device 2 is shown in a further elongated and constricted shape. The distal control body 8 has moved further distally relative to the containing element catheter 6. The user can manipulate the distal control body 8 to extend further distally. As shown, the filament connection 14 is moved further distally and the filament 10 places additional tension on the containing element 4 through the loops 12. The shape of the filament 10 has changed from a generally circular shape to an elliptical or egg shape as the filament 10 also stretches. The containing element 4 has further elongated and further reduced in diameter.

Figure 7:
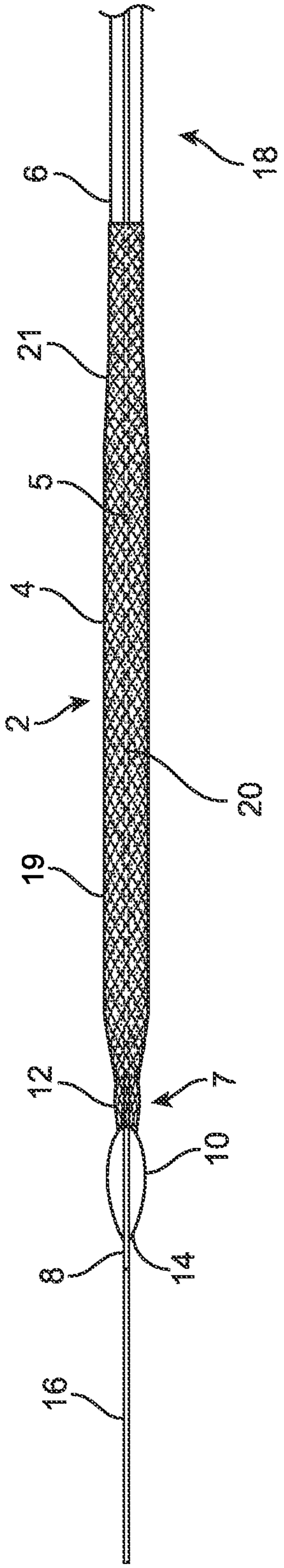
FIG. 7 illustrates the device of FIG. 4 further in a collapsed shape

In FIG. 7, the device 2 is shown in a further elongated and constricted shape. The distal control body 8 has been translated even further distally relative to the containing element catheter 6. This has placed even more distally directed force on the containing element 4 such that it is close to fully elongated and reduced in diameter. As can be seen, the diameter of the containing element 4 is approximating the diameter of the containing element catheter 6 and in some places even less than the diameter of the containing element catheter 6. Additionally, the distal opening 7 of the containing element 4 is tapered to a narrow point where the loops 12 engage with the filament 10. The filament 10 is also elongated and reduced in length across at least one axis. The filament 10 is therefore similarly tapered. As can be seen, the distal opening 7 of the containing element 4 is in a generally closed configuration with no opening remaining. The polymeric membrane at this region is touching itself and creating at least a partial closure between the inside and outside of the containing element. As discussed, in embodiments where the containing element 4 is within a constraining catheter 24 and already in a collapsed configuration, the application of a distally directed force on the distal portion may or may not collapse portions of the containing element 4 further. However, the distally directed force may reduce the outward expansion pressure of the containing element 4 in at least some areas along its length that deceases the overall force for advancing it through and out of the constraining catheter 24.

The use and application of the embodiment of device 2 shown in FIGS. 4-7 will now be discussed. Similar to the embodiments shown in FIGS. 2A-2F, the device 2 can include a constraining catheter 24 that the containing element 4 is inserted through to reach a target vessel and clot. In other embodiments, the device 2 can be used without a constraining catheter 24 positioned in the target vessel, and the device 2 can be navigated for at least a portion of the patient's vasculature without a constraining catheter. In the case of neuro thrombectomy, the device 2 could be inserted through a guide catheter with its distal end in the carotid artery or through a sheath, and the device 2 can be navigated in the constricted shape shown to the middle cerebral artery (MCA). This may allow the containing element catheter 6 to be larger than otherwise possible if a constraining catheter 24 is included. In some embodiments, the device 2 can be inserted through a femoral artery or a radial artery or a direct carotid artery puncture.

With the device 2 in the constricted shape shown in FIG. 7, the device 2 is advanced to the clot 32 in the cerebral artery. The collapsed configuration can be a result of the distally directed force applied by the distal control body 8 to the distal portion, or by the inner lumen 28 of the constraining catheter 24. Once the device 2 is within the cerebral artery and proximal to the clot 32, the user can retract the distal control body 8 to transition the device 2 back through the shapes shown in FIG. 4. As the distal control body 8 is retracted relative to the containing element catheter 6, the tension on the containing element 4 releases and the it begins to expand toward its predetermined shape. The predetermined diameter of the containing element 4 is selected such that it is larger than the diameter of the vessel 34 at least in one or more areas. This causes it to expand until it opposes the vessel 34 in those areas. As the containing element 4 touches the vessel 34, the blood flow is at least partially restricted and may be fully arrested. The distal opening 7 of the containing element 4 opens as the filament 10 retracts. The filament 10 approximates the circumference of the distal opening 7 of the containing element 4 as it retracts and may facilitate in further opening the distal opening 7 of the containing element.

In the embodiment shown where the containing element catheter 6 runs through the entire length of the constraining catheter 24, a suction source 38 can be connected directly to the containing element catheter 6 such that an aspiration path is established through the containing element 4 and withdraws the clot. To remove the device 2 from the patient the containing element catheter 6 and constraining catheter 24 can be pulled proximally and out of the patient. However, additional steps can be employed to ensure that the clot 32 remains within the containing element 4 and does not come out of the distal opening 7. In at least one embodiment, the distal opening 7 can be closed by advancing the distal control body 8 forward similar to the closed configuration shown in FIG. 7. By doing so, the containing element 4 again elongates and constricts around the clot 32 to secure it. Additionally, the distal opening 7 of the containing element 4 may reduce in size as shown in FIG. 7 such the clot 32 cannot exit the containing element 4. At this point the device 2 can be easily removed from the patient and pulled through any other access catheters used. Constricting the containing element 4 may additionally squeeze the clot so that it can be pulled into a guide catheter. The encased clot within the containing element 4 would be less prone to extrude clot fragment or occlude a vascular sheath during removal from said device.

Figure 8:
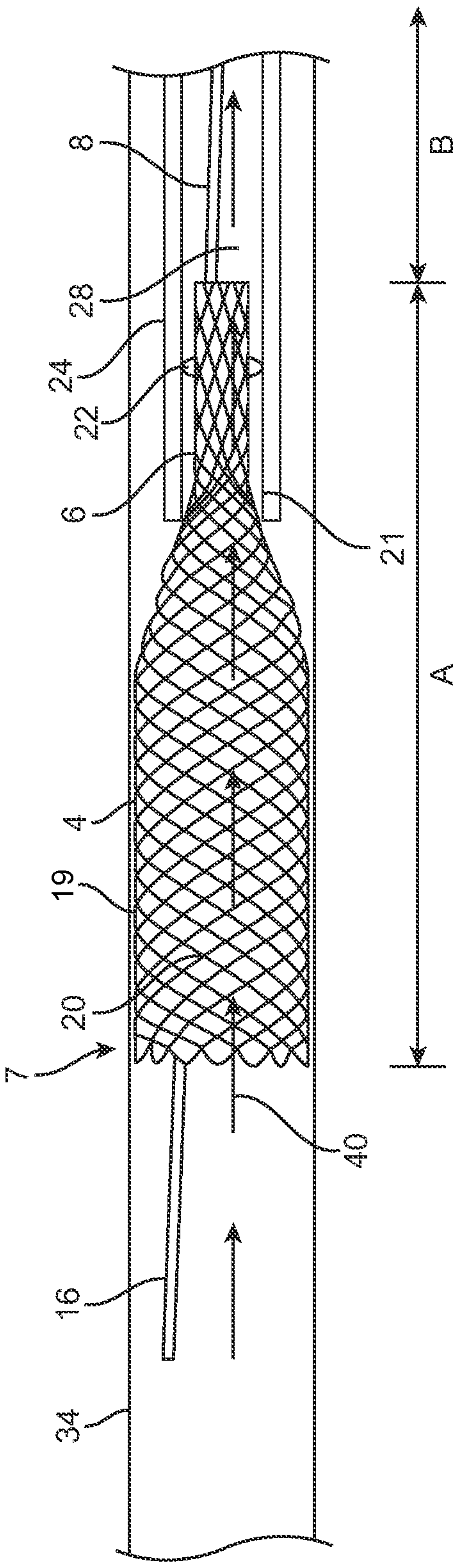
FIG. 8 illustrates another alternative embodiment of a device according to the present disclosure in cross-section.

In FIG. 8, a cross section of device 2 with an aspiration path 40 is shown. The aspiration path 40 begins in the vessel 34 and continues through the distal opening 7 of the containing element 4, then through the interior chamber 20, then through the containing element catheter 6, then through the inner lumen 28 of the constraining catheter 24. The region A defines the aspiration path 40 within the containing element 4, and region B defines the aspiration path within constraining catheter 24. The containing element 4 includes a sealing surface 22 that provides a partial or full seal against the inner lumen 28 of constraining catheter 24. Depending on the clinical application, the region A may be from and including about 0.5 cm to and including about 30 cm long or from and including about 2 cm to and including about 15 cm long or about 4 cm long. The region B will likewise depend on the clinical application and anatomical location of the target site but will generally be from and including about 10 cm to and including about 200 cm or from and including about 50 cm to and including about 150 cm or about 120 cm. As shown in FIG. 3, the proximal end of the constraining catheter 24 may connect to a hemostasis valve 36 and a suction source 38. In this case the aspiration path 40 will additionally continue through these components. In some embodiments, the aspiration path 40 may not pass through the distal opening 7 or a containing element catheter 6. As shown, the containing element catheter 6 can simply be a continuation of the containing element 4 structure. Similarly, the sealing surface 22 can be any number of sealing components or geometries including lip seals, tapered fits, expandable components, or any other suitable method.

Figure 9A:
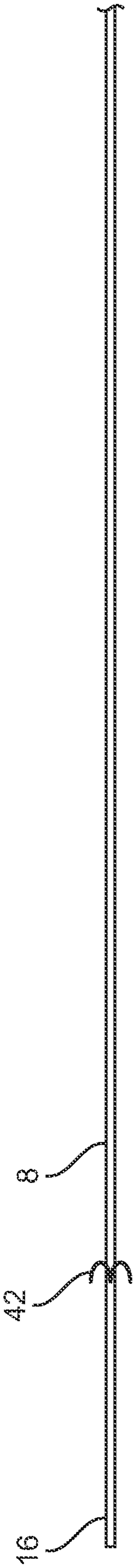
FIG. 9A illustrates another alternative embodiment of a device according to the present disclosure showing a distal control body.
Figure 9B:
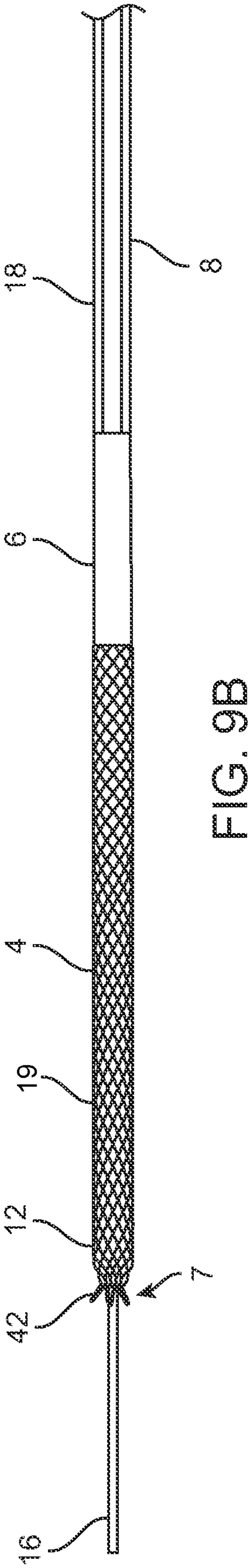
FIG. 9B illustrates the device of FIG. 9A with a containing element attached to the distal control body.
Figure 9C:
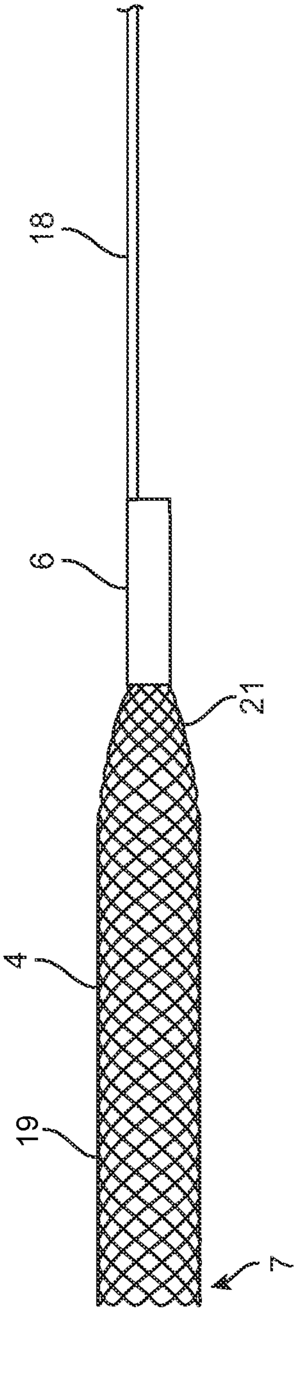
FIG. 9C illustrates the device of FIG. 9A with the containing element with the distal control body removed.

In FIG. 9A, an embodiment of the distal control body 8 is shown. The distal control body 8 has a detachable connection 42 feature that interacts with the containing element 4. The detachable connection 42 feature shown is a set of hooks, but any number of other detachable connections may be contemplated such as graspers and snares. In FIG. 9B, the distal control body 8 is removably attached to an embodiment of the containing element 4 using the detachable features 42. The hooks are engaged with the loops 12 and the distal control body 8 can elongate the containing element 4 by applying a distally directed force that pulls the containing element 4 via the detachable connection 42. The device 2 can be inserted through a constraining catheter 24 in this configuration and delivered to the target vessel. The distally directed force applied by the detachable connection 42 to distal portion of the containing element 4 can also reduce the outward expansion pressures of the containing element 4 in embodiments where it is delivered through a constraining catheter 24. In FIG. 9C, the device 2 is shown with the distal control body 8 withdrawn and the detachable connection 42 detached from the containing element 4. In the embodiment shown, the distal control body 8 can be simply withdrawn proximally and the loops 12 can unhook from the detachable connection 42. In other embodiments with active detachable connections 42 like graspers, the containing element 4 can be actively released. At this point the device 2 is in an expanded configuration in the target vessel and can be used in the manner described herein. In other embodiments, a filament 10 or suture can be attached to the distal opening 7 of the containing element 4 and provide a connection point for the detachable connection 42. In some embodiments, the distal control body 8 may be constructed like a microcatheter to provide sufficient stiffness for elongating the containing element 4 and may allow for various guidewires to be inserted into the microcatheter to adjust the stiffness of the device 2.

In some embodiments, the detachable connection 42 feature can be accomplished with vacuum. The distal control body 8 can have a lumen, similar to a microcatheter, that forms an aspiration path and can have one or more holes along its side wall. This can allow the distal control body 8 to apply a radial suction force onto the interior chamber 20 or distal opening 7. In this manner, the distal control body 8 can collapse and elongate the containing element 4 using suction to hold it against the side walls of the distal control body 8. In other embodiments, the detachable connection 42 can be a cone or cover that surrounds the distal portion of containing element 4 such that the expandable interior chamber 20 is held in a collapsed configuration at that location.

Figure 10:
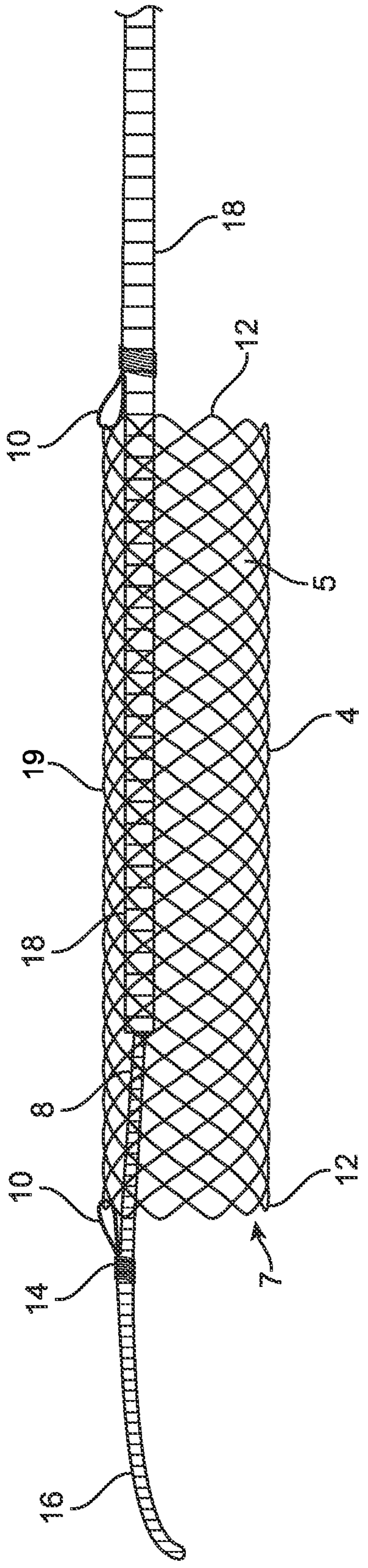
FIG. 10 illustrates another embodiment of a device according to the present disclosure, the device including each of a distal control body and proximal control body.

In FIG. 10 an alternate embodiment of device 2 is shown with a proximal control body 18 that runs at least partially through the lumen of the containing element 4 and is attached to the proximal end of the device 2 with a filament 10. In the embodiment shown, the filament 10 goes through one of the loops 12 and is then attached to the outer surface of the proximal control body 18 but any number of other connection methods are possible. It should be appreciated that the filament 10 can be woven fully circumferentially around the proximal end of the containing element 4. The proximal control body 18 extends forward into the interior chamber 20 of containing element 4. Extending out of the proximal control body 18 is a distal control body 8 that is connected to the distal opening 7 of the containing element 4 through the filament 10 woven through one or more of the loops 12. In this manner, the containing element 4 can be elongated and constricted by pushing the distal control body 8 distally out of the proximal control body 18 which applies a distally directed force to the containing element 4, and can be shortened and enlarged by translating the distal control body 8 proximally. The distal control body 8 and proximal control body 18 can be constructed from any number of elements described herein such as compression coils, composite braid structures, laser cut tubes, polymer tubes, or any other suitable method. This embodiment of device 2 could use similarly to other embodiments described herein including but not limited to clot retrieval and blood flow arrest. The relative motion between the distal control body 8 and proximal control body 18 control the shape and can transition the containing element 4 to various configurations. If the containing element 4 is inserted through a constraining catheter 24, the outward expansion pressure of the containing element 4 can be reduced by applying a force between distal control body 8 and proximal control body 18 that promotes collapse of the containing element 4.

Figures 11A, 11B, 11C:
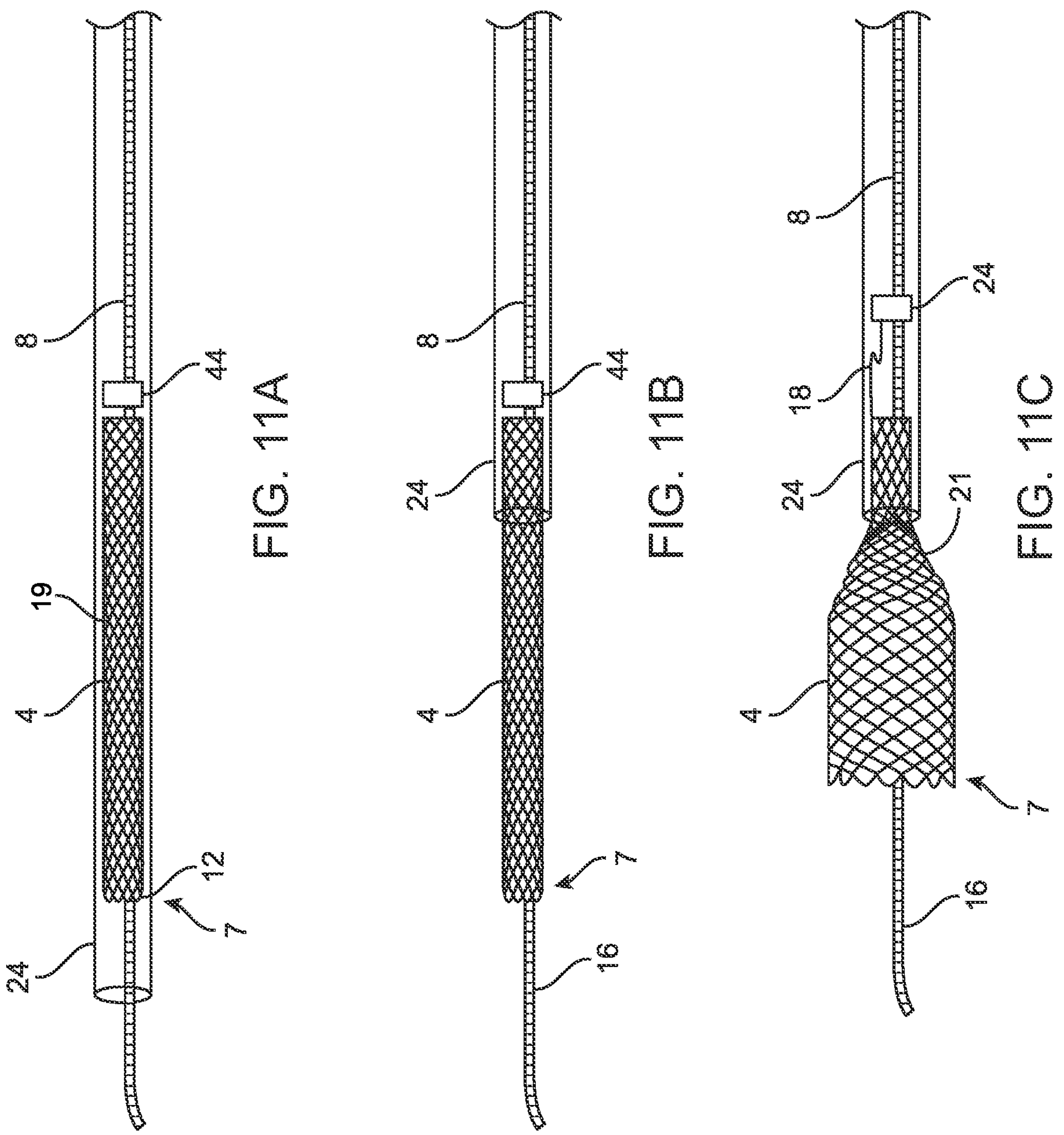
FIG. 11A illustrates yet another embodiment of a device according to the present disclosure with a containing element collapsed within a constraining catheter.
FIG. 11B illustrates the device of FIG. 11A with the containing element partially deployed.
FIG. 11C illustrates the device of FIG. 11A with the containing element in an expanded configuration.

In FIGS. 11A-11C, an embodiment of the device 2 which includes a proximal pushing body 44. The proximal pushing body 44 can be a short section of tubing, a plastic bump, a shark fin, or any other suitable geometry configured to push the proximal end of the containing element 4. The proximal pushing body 44 is connected to the distal control body 8 and during delivery, as shown in FIG. 11A, it pushes on the proximal end of the containing element 4 while the distal control body 8 also pulls on the distal opening 7 of the containing element 4 through the filament 10. In FIG. 11A, a small gap is shown between the proximal pushing body 44 and the proximal end of containing element 4, but it should be appreciated that these could also be in intimal contact when the proximal pushing body 44 is pushing against it.

In FIG. 11B, the containing element 4 has reached the distal end of the constraining catheter 24 at the target site. The containing element 4 extends out of the constraining catheter 24.

In FIG. 11C, the distal control body 8 can be retracted such that the distal opening 7 of the containing element 4 opens and this also may move the proximal pushing body 44 proximally so it is not blocking the inner lumen of the containing element 4 through which aspiration flows. The device 2 may also include a proximal control body 18 connected at the proximal end of the containing element 4 and to either the proximal pushing body 44 or any portion of the distal control body 8. The proximal control body 18 length can be such that upon further retraction of the distal control body 8, the device 2 moves proximally since it is being pulled by the proximal control body 18 at its proximal end. This can be timed such that the opening at the distal opening 7 of the containing element 4 is closed by inverting inward just before the device begins to be retracted into the constraining catheter 24. In this manner, the user interface is simplified so that the user only controls the motion of the distal control body 8 but can use it to deliver the device 2 by pushing the distal control body 8, open the containing element 4 by pulling the distal control body 8 a given amount, close the distal opening 7 of the containing element 4 after clot ingestion by retracting the distal control body 8 another amount, and then remove the device 2 by retracting the distal control body 8 even further, possibly while retracting the constraining catheter 24 at the same time.

Figure 12:
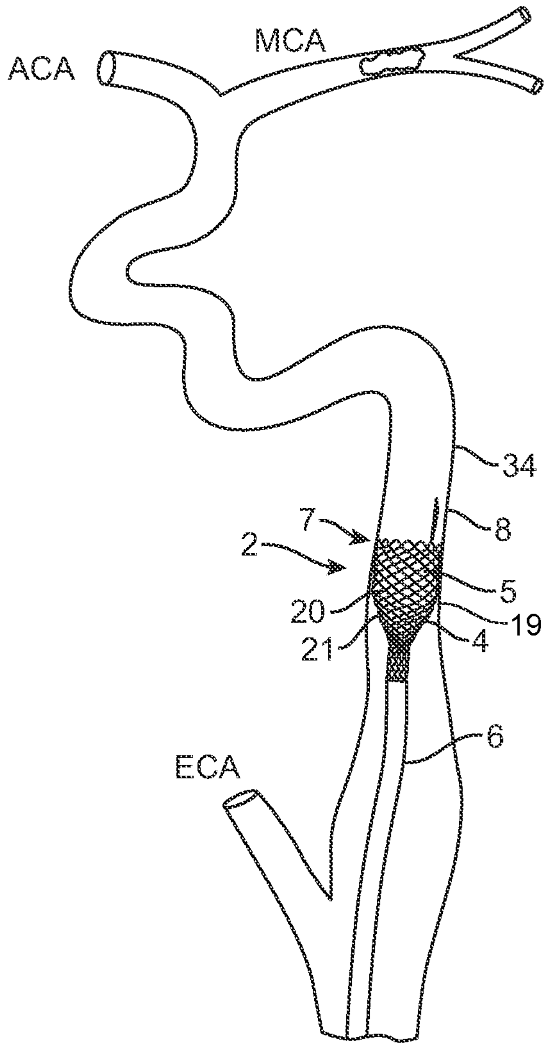
FIG. 12 illustrates an embodiment of a device according to the present disclosure used for flow control.

In FIG. 12, an embodiment of the device 2 is shown that can be used for flow arrest. Much description has been given to thrombectomy procedures where clot is removed but that is not intended to limit the scope or use of the device 2 to such procedures. In some embodiments, the device 2 may be used primarily for restricting blood flow in vessels. In FIG. 12, the embodiment of device 2 may be used as a substitute for a balloon guide catheter during thrombectomy procedure. The device 2 is shown with an inner diameter from and including about 6 Fr to and including about 9 Fr and may be delivered into the carotid artery. The membrane 5 on the outer surface of the interior chamber 20 of containing element 4 can block blood flow through the vessel while a thrombectomy procedure is performed using other devices that run coaxially through the center and out the distal opening 7 of the device 2. The containing element catheter 6 in this embodiment is long enough to extend out through the patient and can be the central lumen through which other aspiration catheters and stent retrievers can be placed. The containing element 4 is shorter since it does not need to contain clot and can therefore primarily be made of a tapered region 21 with a distal opening 7 region that is in contact with the vessel 34. Once in place, a distal access catheter can be advanced through the containing element 4 and to the clot in the MCA to perform thrombectomy procedures. The device 2 can block blood flow past the distal opening 7 which reduces the risk of the clot fragmenting. In some embodiments, similar closure mechanisms and transitions described herein can be used to contain the clot after it has been retrieved by aspiration or a stent retriever.

In some embodiments, hydraulic force can be used to deliver the device 2 to the target site within a constraining catheter. For example, the distal opening 7 of the device 2 can be closed so that once it is inserted into the constraining catheter and fluid is injected into the constraining catheter, the device 2 is urged forward by hydraulic force. The advancement of the device 2 could therefore be controlled by the pressure and amount of fluid injected into the constraining catheter.

In some embodiments, a suction source 38 may be used to collapse the expandable interior chamber 20 of the containing element 4. For example, the containing element catheter 6 can be connected to the suction source 38 such that a vacuum can be generated within the interior chamber as the containing element 4 is elongated. The distal opening 7 of the containing element 4 can be in a closed configuration and therefore the applied vacuum can assist in keeping the containing element 4 elongated. A distal plug element could alternatively be used to maintain a closed seal at the distal opening.

In some embodiments, the distal control body 8 or proximal control body 18 can be used to inject or withdraw fluids from the patient. The distal control body 8 can be a single channel tube or have additional lumens that allow for fluid communication by the user from the proximal end to the distal end. For example, the user may inject contrast agents through the distal control body 8 that allow the user to see where the distal end of the device 2 is or if it has passed the clot. Alternatively, the user may inject fluid distally beyond the clot to create a hydraulic pressure gradient that urges the clot toward the distal opening 7 of the containing element 4. In still other embodiments, the user may aspirate fluid through the distal control body 8 which may be used to grab the clot. The regional flow arrest created by the containing element 4 membrane 5 opposed to the vessel wall may allow for small volumes of contrast to identify clot 32 location and vascular anatomy due to flow stasis during contrast injection.

Alternatively, it may be used to limit blood flow when gluing or embolizing arteriovenous malformations (AVMs), high flow fistulas, or aneurysms. In other embodiments, the device 2 can be deployed in the internal carotid artery (ICA) to restrict blood flow during any number of neurovascular procedures including thrombectomy or stenting procedures. In other embodiments, the device 2 may be used to temporarily restrict blood flow during treatment of vascular perforation or vessel injury to stop life threatening hemorrhage. In this embodiment, the device 2 may be used to restrict blood flow but not entirely arrest it such that extremities still receive some blood flow but the patient's blood loss is controlled within a safe limit.

The device 2 can have a variety of shapes and sizes serving as a platform for any type of thrombectomy, embolectomy, or foreign body, calculi or tissue removal in any part of the body or vessel. The device 2 may provide proximal support and purchase for placement of distal devices such as rheolytic catheters, suction devices, graspers, balloons such as a Fogarty balloon, wire snares, stent retrievers, etc. for any size tube or vessel including arteries, veins, ureters, airways, bile ducts, and hollow viscous for retrieval of material. The devices and methods described within may be used in any number of other surgical procedure. For example, peripheral blood clots may be likewise removed with such a system. This could include but not limited to deep venous thrombosis, pulmonary emboli, clotted hemodialysis grafts or peripheral arterial thromboemboli, including the mesenteric and peripheral vascular tree. The expanded device provides the operator an anchor and purchase to the desired vascular tree for further intervention as needed.

Any number of other suitable applications may use such a device 2 for contained removal of a tissue, foreign body, calculi or other objects within a tubular contained space or even within non-tubular or non-contained spaces.

The device 2 can go through any number of other catheters in order to be advanced to the target vessel. For example, in some embodiments the device 2 can be inserted through a 6 Fr guide sheath that has already been advanced to a cerebral artery such that the device 2 is merely following within the guide sheath. In other embodiments, the device 2 can be advanced to a cerebral artery without the need for a guide sheath that has already accessed the cerebral artery. This may simplify the procedure and reduce the overall size constraints on the device 2 since it does not need to fit within a guide sheath. In this embodiment, the device 2 may be inserted through a femoral sheath or radial sheath to access the vasculature but after placement through this sheath it is no longer within another catheter or sheath. In still other embodiments, the device 2 may be inserted through a sheath that provides access part way along the patient's vasculature such as to the internal carotid artery. Any number of other combinations of catheters and sheath are contemplated herein.

In some embodiments, the device 2 may contain all or only a portion of the devices described herein. For example, the device 2 may include a clot engagement element such as a stent retriever or aspiration catheter. Alternatively, the device 2 may only include the containing element 4 and filament 10 and the device 2 may be used with an existing off-the-shelf available stent retriever. In such an embodiment, the containing element 4 and filament 10 may be sized to accept such a retriever. The device 2 may be inserted into the body after the stent retriever has been deployed and captured the clot, potentially utilizing a Rapid Exchange technique. In this way it is a stand-alone system for capturing the clot that includes using other clot engagement elements. In some embodiments, the distal control body 8 can be a tube that enables an over-the-wire technique or Rapid Exchange technique for tracking the containing element 4 along the stent retriever wire, using the stent retriever as an anchor. Any number of other configurations of the devices described herein are contemplated.

The devices and methods described herein can be used for any number of clinical applications where local flow arrest or clot removal or clot containment are desired. For example, the invention may be used for removing clot from a cerebral or carotid artery to treat an acute ischemic stroke. It may also be used for treatment of pulmonary embolisms, deep vein thrombosis (DVT) both chronic and acute, arterial thrombectomy, stone removal, blocking flow during radioactive fluid injections or selective embolization maneuvers. The device could be deployed in any number of vascular targets such as veins and arteries. A particular advantage of the invented device and method is that aspiration can be performed using a relatively small containing element catheter 6 or constraining catheter 24 where the containing element 4 creates a large lumen at the front of the catheter and fully contains the clot during removal from the patient.

The names and labels applied to the various components and parts should not be considered limiting to the scope of the invented device and method. For example, the term filament used herein may be interchangeably used with snare, wire, ribbon, coil, elongate member, or any other suitable term. The term catheter is used to describe an elongate member with a distal and proximal end with a lumen extending there through. The terms intermediate catheter, constraining catheter, filament catheter, guide catheter, and micro catheter may often be used interchangeably. The term container may often be interchangeably used with bag, containing element, container element, pouch, or any other suitable term. When referring to the opening of the distal opening, the terms releasing, deploying, opening, and expanding may be used interchangeably. When referring to the closure of the distal opening the terms cinching, closing, constraining, collapsing, constricting, snaring, or any other suitable term may often be used interchangeably. When referring to the radial constraining of the containing element by catheters, vessels, or filaments, the terms constraining, restricting, containing, collapsing or constricting may also often be used interchangeably. The term distal or distal portion generally refers to areas of the device situated away from the center of the device in the direction of blood flow while the term proximal generally refers to areas of the device situated away from the center of the device in the opposite direction of blood flow. The term distal opening can refer to the distal portion of the containing element within about 1-10 mm of the distal most aspect.

Although embodiments of various methods and devices are described herein in detail with reference to certain versions, it should be appreciated that other versions, embodiments, methods of use, and combinations thereof are also possible. Therefore, the spirit and scope of the appended claims should not be limited to the description of the embodiments contained herein.

What is claimed is:

1. A system for removing occlusive material from vessels, the system comprising:

a catheter defining a lumen; and a material removal device including:

a containing element including a distal opening and an outer wall portion, wherein the outer wall portion defines an expandable interior chamber; and a distal control body extending through the distal opening, wherein the distal control body is coupled to a distal portion of the containing element, wherein the distal control body is configured to apply distally directed forces on the distal opening by translating the distal control body relative to the containing element, wherein, when the material removal device is disposed within the catheter and a distal force is applied to the containing element by distally translating the distal control body, the containing element deploys from the catheter; and wherein when the containing element is deployed from the catheter, applying a second distal force by distally translating the distal control body transitions the containing element into a collapsed configuration.

2. The system of claim 1, wherein the expandable chamber is biased into an expanded configuration such that, when deployed from the catheter, the containing element transitions into the expanded configuration.

3. The system of claim 1, wherein, when the containing element is in an expanded configuration within a vessel, the outer wall portion contacts a wall of the vessel and the containing element restricts antegrade flow in the vessel.

4. The system of claim 1, wherein, the expandable interior chamber has an outward expansion pressure from and including about 760 mmHg to and including about 1000 mmHg.

5. The system of claim 1 further comprising a suction source in fluid communication with the lumen of the catheter.

6. The system of claim 5, wherein, when the containing element is deployed from the catheter, an aspiration path extends from the distal opening of the containing element to the suction source, the aspiration path extending through each of the expandable chamber and the lumen of the catheter.

7. The system of claim 6, wherein a portion of the aspiration path through the containing element is from and including 1 cm to and including 20 cm.

8. The system of claim 1, wherein, when the containing element is deployed from the catheter and in an expanded configuration, a proximal portion of the containing element remains within the lumen of the catheter.

9. The system of claim 1, wherein a proximal portion of the containing element includes a sealing surface that seals against the lumen of the catheter.

* * * * *